US011890266B2

(12) United States Patent
Ashby

(10) Patent No.: US 11,890,266 B2
(45) Date of Patent: Feb. 6, 2024

(54) OPHTHALMIC COMPOSITIONS INCLUDING LEVODOPA, AN ANTIOXIDANT AND AN AQUEOUS CARRIER

(71) Applicant: University of Canberra, Bruce (AU)

(72) Inventor: Regan Scott Ashby, Franklin (AU)

(73) Assignee: UNIVERSITY OF CANBERRA, Bruce (AU)

( * ) Notice: Subject to any disclaimer, the term of this patent is extended or adjusted under 35 U.S.C. 154(b) by 348 days.

(21) Appl. No.: 17/103,709

(22) Filed: Nov. 24, 2020

(65) Prior Publication Data
US 2021/0077443 A1    Mar. 18, 2021

Related U.S. Application Data

(62) Division of application No. 16/092,291, filed as application No. PCT/AU2017/050310 on Apr. 10, 2017, now Pat. No. 10,874,629.

(30) Foreign Application Priority Data

Apr. 11, 2016 (AU) ............................... 2016901339

(51) Int. Cl.
*A61K 31/198* (2006.01)
*A61K 31/375* (2006.01)
(Continued)

(52) U.S. Cl.
CPC .......... *A61K 31/198* (2013.01); *A61K 9/0019* (2013.01); *A61K 9/0048* (2013.01);
(Continued)

(58) Field of Classification Search
CPC .. A61K 31/198; A61K 9/0019; A61K 9/0048; A61K 31/375; A61K 45/06
See application file for complete search history.

(56) References Cited

U.S. PATENT DOCUMENTS 5,385,939 A    1/1995 Laties
5,814,638 A    9/1998 Lee
(Continued)

FOREIGN PATENT DOCUMENTS

CN    1 569 219 A    1/2005
CN    100998586 A    7/2007
(Continued)

OTHER PUBLICATIONS

Toutellotte et al., Arch Neurol, vol. 37 (1980) p. 723-726 (Year: 1980).*

(Continued)

*Primary Examiner* — San Ming R Hui
(74) *Attorney, Agent, or Firm* — Knobbe, Martens, Olson & Bear, LLP

(57) ABSTRACT

Pharmaceutical ocular compositions include levodopa, an antioxidant and an aqueous carrier. A wide selection of antioxidants can be included in the compositions, such as ascorbic acid, phenolic acids, sorbic acid, sodium bisulfite, sodium metabisulfite, acetyl cysteine, sodium thiosulfate, ethylene diamine tetraacetic acid, sodium nitrite, ascorbyl stearate, ascorbyl palmitate, alpha-thioglycerol, erythorbic acid, cysteine hydrochloride, citric acid, tocopherol or vitamin E, tocopherol acetate, dibutylhydroxytoluene, soybean lecithin, sodium thioglycolate, butylhydroxyanisole, propyl gallate, uric acid, melatonin, and thiourea, as well as salts and combinations of these antioxidants.

21 Claims, 14 Drawing Sheets

(51) Int. Cl.
*A61K 45/06* (2006.01)
*A61P 27/10* (2006.01)
*A61K 9/00* (2006.01)

(52) U.S. Cl.
CPC ............ *A61K 31/375* (2013.01); *A61K 45/06* (2013.01); *A61P 27/10* (2018.01)

(56) References Cited

U.S. PATENT DOCUMENTS

| | | | |
|---|---|---|---|
| 8,735,382 | B2 | 5/2014 | Segrell |
| 2004/0220270 | A1 | 11/2004 | John |
| 2010/0298428 | A1 | 11/2010 | Yacoby-Zeevi |
| 2014/0036225 | A1 | 2/2014 | Chehab |
| 2019/0151270 | A1 | 5/2019 | Ashby |

FOREIGN PATENT DOCUMENTS

| | | |
|---|---|---|
| CN | 101022784 A | 8/2007 |
| JP | 2005-533082 A | 11/2005 |
| JP | 2007-504143 A | 3/2007 |
| JP | 2013-502460 A | 1/2013 |
| WO | WO 94/25018 A1 | 11/1994 |
| WO | WO 2004/002399 A2 | 1/2004 |
| WO | WO 2005/023185 A2 | 3/2005 |
| WO | WO 2006/006929 A1 | 1/2006 |
| WO | WO 2009/003226 A1 | 1/2009 |
| WO | WO 2009/114740 A2 | 9/2009 |
| WO | WO 2011/025734 A1 | 3/2011 |
| WO | WO 2015/009533 A1 | 1/2015 |
| WO | WO 2015/095257 A2 | 6/2015 |
| WO | WO 2015/200361 A1 | 12/2015 |
| WO | WO 2016/036308 A1 | 3/2016 |
| WO | WO 2016/109457 A1 | 7/2016 |

OTHER PUBLICATIONS

Kankkunen et al., European Journal of Pharmaceutical Sciences 16 (2002) 273-280. (Year: 2002).*
International Search Report & Written Opinion, dated Jun. 23, 2017, in International Application No. PCT/AU2017/050310.
Karouta, C., et al., Correlation Between Light Levels And The Development Of Deprivation Myopia, Investigative Ophthalmology & Visual Science, vol. 56, pp. 299-309, 2015.
Mao, J., et al., Levodopa Inhibits the Development of Form-Deprivation Myopia in Guinea Pigs, Optometry And Vision Science, vol. 87, No. 1, pp. 53-60, 2010.
Mao, J., et al., Exogenous Levodopa Increases The Neuro Retinal Dopamine Of Guinea Pig Myopic Eyes In Vitro, Eye Science, vol. 26, No. 4, pp. 211-216, 2011.
International Preliminary Report on Patentability, dated Oct. 25, 2018, in International Patent Application No. PCT/AU2017/050310.
Dong, F., et al., Inhibition of experimental myopia by a dopamine agonist: different effectiveness between form deprivation and hyperopic defocus in guinea pigs, Molecular Vision, vol. 17, pp. 2824-2834, 2011.
Gao, Q., et al., Effects of direct intravitreal dopamine injections on the development of lid-suture induced myopia in rabbits, Graefe's Arch Clin Exp Ophthalmol, vol. 244, pp. 1329-1335, 2006.
Gaudana, R., et al., Ocular Drug Delivery, The AAPS Journal, vol. 12, No. 3, pp. 348-360, 2010.
Iuvone, P.M., et al., Effects of Apomorphine, a Dopomine Receptor Agonist, on Oculor Refraction and Axial Elongation in a Primate Model of Myopia, Investigative Ophthalmology and Visual Science, vol. 32, No. 5, pp. 1674-1677, 1991.
Lind, G.J., et al., Muscarinic Acetylcholine Receptor Antagonists Inhibit Chick Scleral Chondrocytes, Investigative Ophthalmology and Visual Science, vol. 39, No. 12, pp. 2217-2231, 1998.
Schmid, K.L., et al., The effects and interactions of GABAergic and dopaminergic agents in the prevention of form deprivation myopia by brief periods of normal vision, Experimental Eye Research, vol. 110, pp. 88-95, 2013.
Smith, M.J., et al., Controlling myopia progression in children and adolescents, Adolescent Health, Medicine and Therapeutics, vol. 6, pp. 133-140, 2015.
Stone, R.A., et al., GABA, Experimental Myopia, and Ocular Growth in Chick, Investigative Ophthalmology and Visual Science, vol. 44, No. 9, pp. 3933-3946, 2003.
Walline, J.J., et al., Interventions to slow progression of myopia in children, Cochrane Database Syst Rev, vol. 12: CD004916, 2011.

* cited by examiner

OPHTHALMIC COMPOSITIONS INCLUDING LEVODOPA, AN ANTIOXIDANT AND AN AQUEOUS CARRIER

This application is a Divisional Application of U.S. application Ser. No. 16/092,291, filed Oct. 9, 2018, which is the U.S. National Stage Application under 35 U.S.C. § 371 of International Application No. PCT/AU2017/050310, filed Apr. 10, 2017, designating the U.S. and published in English as WO 2017/177262 A1 on Oct. 19, 2017, which claims priority to Australian Provisional Application No. 2016901339 entitled "Compositions and Methods of Use" filed on 11 Apr. 2016, the entire content of which is hereby incorporated herein by reference in its entirety.

FIELD OF THE INVENTION

This invention relates generally to compositions comprising levodopa and an antioxidant for inhibiting the development or progression of visual disorders inclusive of visual disorders associated with diabetic retinopathy or Parkinson's disease, and myopia.

BACKGROUND OF THE INVENTION

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavor to which this specification relates.

Myopia, commonly known as short-sightedness, is a visual disorder caused by excessive elongation (axial length) of the eye during development. Myopia is the leading cause of low vision and the most common eye disease worldwide, with some estimating that myopia may affect up to one-third of the world's population by the end of the decade. Prevalence is at its highest in urban East Asia, where in many parts approximately 80-90% of school leavers are myopic.

The prevalence of myopia appears to be strongly associated with the amount of time spent outdoors in bright light. Specifically, epidemiological studies have reported that time spent outdoors is a potent protective factor against the development of myopia in children. Animal studies have indicated that this protective effect appears to be associated with light induced increases in dopamine levels within the eye.

Attempts are being made to reduce the onset and progression of myopia, including increasing the amount of time that children spend outdoors in bright light. However, in many parts of the world geographical location and local climate restrictions may prevent light levels from being strong enough or exposure time from being long enough to protect against myopia. Furthermore, social and cultural barriers may prevent increasing the time children spend outdoors as it is perceived as hindering education and academic progression.

Current treatment options to reduce the progression of myopia include optical approaches, such as single vision lenses, multifocal lenses, peripheral lenses and orthokeratology; and pharmaceutical agents, such as atropine and pirenzepine. With regards to optical approaches, findings from clinical trials have been mixed, with the majority of optical approaches showing limited to no long-term effect on the rate of myopia progression. Optical approaches are also not targeted at preventing the onset of myopia, only its progression. Traditionally, treatment with pharmaceutical agents, such as atropine, have been most effective at reducing the rate of myopia progression. However, the widespread use of atropine has been inhibited by concerns about post-treatment rebound effects, as well as the significant short- and long-term adverse effects.

Accordingly, new therapies for inhibiting the development or progression of a visual disorder such as myopia are required.

SUMMARY OF THE INVENTION

The present invention is predicated in part on the discovery that aqueous formulations of levodopa in combination with an antioxidant can penetrate ocular tissues and significantly elevate intraocular dopamine levels to thereby inhibit the development or progression of a visual disorder in a subject, particularly a visual disorder involving reduced dopamine levels in the eye, such as a visual disorder associated with diabetic retinopathy or Parkinson's disease, or myopia.

Levodopa is a naturally occurring precursor to the neurotransmitters dopamine, epinephrine and norepinephrine. Presently, levodopa is orally administered for the treatment of Parkinson's disease and elevates dopamine levels within the central nervous system and, to a lesser extent, systemically. However, oral administration of levodopa is not applicable to the treatment of visual disorders as it is undesirable to significantly elevate dopamine levels within the brain of a subject with a visual disorder and oral administration requires large doses of levodopa due to systemic distribution.

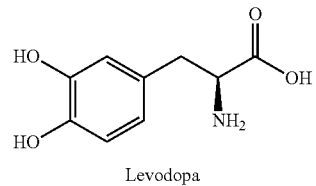 [SMILES: N[C@@H](Cc1ccc(O)c(O)c1)C(=O)O]

Levodopa

In one aspect, the present invention provides a pharmaceutical ocular composition, comprising, consisting or consisting essentially of levodopa, an antioxidant and an aqueous carrier. The inventors have found that it is desirable to formulate levodopa in an aqueous carrier so that it penetrates ocular tissues and is available for elevating intraocular dopamine levels.

In another aspect of the present invention, there is provided a composition for inhibiting the development or progression of a visual disorder, comprising, consisting or consisting essentially of levodopa, an antioxidant and an aqueous carrier. The composition may also be used for treating or preventing a visual disorder.

In yet another aspect of the present invention, a method is provided for inhibiting the progression or development of a visual disorder in a subject, comprising administering to the subject the composition of the invention. In some embodiments, the visual disorder is treated in the subject. In other embodiments, the visual disorder is prevented in the subject.

Another aspect of the present invention provides a use of the composition of the invention for inhibiting the progression or development of a visual disorder in a subject.

In a further aspect, the present invention provides a composition of the invention for use in inhibiting the progression or development of a visual disorder in a subject.

The present invention also provides the use of the composition of the invention in the manufacture of a medicament for inhibiting the progression or development of a visual disorder in a subject.

In a still further aspect of the present invention, there is provided a method of preparing the composition of the invention, comprising dissolving levodopa in the aqueous carrier at a pH in the range of from 0.5 to 2, adding the antioxidant to the composition and adjusting the pH of the composition to a pH in the range of from 5 to 8.

Another aspect of the present invention provides a pharmaceutical ocular composition formulated for topical administration to the eye, comprising, consisting or consisting essentially of levodopa, an antioxidant and an aqueous carrier.

In yet another aspect, the present invention provides a topical composition for inhibiting the progression or development of a visual disorder, comprising, consisting or consisting essentially of levodopa, an antioxidant and an aqueous carrier.

In a further aspect, the present invention provides a method for inhibiting the progression or development of a visual disorder in a subject, comprising administering to the subject a composition comprising, consisting or consisting essentially of levodopa, an antioxidant and an aqueous carrier, wherein the visual disorder is selected from a visual disorder associated with diabetic retinopathy, a visual disorder associated with Parkinson's disease, and myopia.

In still a further aspect, there is provided a use of a composition comprising, consisting or consisting essentially of levodopa, an antioxidant and an aqueous carrier for inhibiting the progression or development of a visual disorder in a subject, wherein the visual disorder is selected from a visual disorder associated with diabetic retinopathy, a visual disorder associated with Parkinson's disease, and myopia.

In another aspect, the present invention provides a composition comprising, consisting or consisting essentially of levodopa, an antioxidant and an aqueous carrier for use in inhibiting the progression or development of a visual disorder in a subject, wherein the visual disorder is selected from a visual disorder associated with diabetic retinopathy, a visual disorder associated with Parkinson's disease, and myopia.

In yet another aspect, there is provided a use of a composition comprising, consisting or consisting essentially of levodopa, an antioxidant and an aqueous carrier in the manufacture of a medicament for inhibiting the progression or development of a visual disorder in a subject, wherein the visual disorder is selected from a visual disorder associated with diabetic retinopathy, a visual disorder associated with Parkinson's disease, and myopia.

In a further aspect, the invention provides a method for inhibiting the progression or development of a visual disorder in a subject, comprising administering to the subject a composition comprising, consisting or consisting essentially of levodopa or a pharmaceutically acceptable salt and/or solvate thereof, or prodrug thereof, an antioxidant and an aqueous carrier, wherein the visual disorder is selected from a visual disorder associated with diabetic retinopathy, a visual disorder associated with Parkinson's disease, and myopia.

In still a further aspect, there is provided a use of a composition comprising, consisting or consisting essentially of levodopa or a pharmaceutically acceptable salt and/or solvate thereof, or prodrug thereof, an antioxidant and an aqueous carrier for inhibiting the progression or development of a visual disorder in a subject, wherein the visual disorder is selected from a visual disorder associated with diabetic retinopathy, a visual disorder associated with Parkinson's disease, and myopia.

In another aspect, the present invention provides a composition comprising, consisting or consisting essentially of levodopa or a pharmaceutically acceptable salt and/or solvate thereof, or prodrug thereof, an antioxidant and an aqueous carrier for use in inhibiting the progression or development of a visual disorder in a subject, wherein the visual disorder is selected from a visual disorder associated with diabetic retinopathy, a visual disorder associated with Parkinson's disease, and myopia.

In yet another aspect, there is provided a use of a composition comprising, consisting or consisting essentially of levodopa or a pharmaceutically acceptable salt and/or solvate thereof, or prodrug thereof, an antioxidant and an aqueous carrier in the manufacture of a medicament for inhibiting the progression or development of a visual disorder in a subject, wherein the visual disorder is selected from a visual disorder associated with diabetic retinopathy, a visual disorder associated with Parkinson's disease, and myopia.

In particular embodiments, the visual disorder is myopia.

In still another aspect, there is provided a method for inhibiting the progression or development of a visual disorder in a subject, comprising administering to the subject a composition comprising, consisting or consisting essentially of levodopa or a pharmaceutically acceptable salt and/or solvate thereof, or prodrug thereof, and a pharmaceutically acceptable carrier, wherein the visual disorder is selected from a visual disorder associated with diabetic retinopathy, a visual disorder associated with Parkinson's disease, and myopia.

In a further aspect, there is provided a use of a composition comprising, consisting or consisting essentially of levodopa or a pharmaceutically acceptable salt and/or solvate thereof, or prodrug thereof, and a pharmaceutically acceptable carrier for inhibiting the progression or development of a visual disorder in a subject, wherein the visual disorder is selected from a visual disorder associated with diabetic retinopathy, a visual disorder associated with Parkinson's disease, and myopia.

In another aspect, the present invention provides a composition comprising, consisting or consisting essentially of levodopa or a pharmaceutically acceptable salt and/or solvate thereof, or prodrug thereof, and a pharmaceutically acceptable carrier for use in inhibiting the progression or development of a visual disorder in a subject, wherein the visual disorder is selected from a visual disorder associated with diabetic retinopathy, a visual disorder associated with Parkinson's disease, and myopia.

In yet another aspect, there is provided a use of a composition comprising, consisting or consisting essentially of levodopa or a pharmaceutically acceptable salt and/or solvate thereof, or prodrug thereof, and a pharmaceutically acceptable carrier in the manufacture of a medicament for inhibiting the progression or development of a visual disorder in a subject, wherein the visual disorder is selected from a visual disorder associated with diabetic retinopathy, a visual disorder associated with Parkinson's disease, and myopia.

In some embodiments, the composition comprises, consists or consists essentially of levodopa and a pharmaceutically acceptable carrier. In particular embodiments, the pharmaceutically acceptable carrier is an aqueous carrier.

In particular embodiments, the visual disorder is myopia.

BRIEF DESCRIPTION OF THE DRAWINGS

FIG. 13A represents stained retinae from the contralateral control eye of a chick, wherein the other eye is fitted with a translucent diffuser to induce FDM; FIG. 13B represents stained retinae from the eye of a chick fitted with a translucent diffuser to induce FDM; FIG. 13C represents stained retinae from the contralateral control eye of a chick, wherein the other eye is fitted with a translucent diffuser to induce FDM and is treated with daily topical administration of a composition comprising 0.3% w/v levodopa; FIG. 13D represents stained retinae from the eye of a chick fitted with a translucent diffuser to induce FDM and treated with daily topical administration of a composition comprising 0.3% w/v levodopa; FIG. 13E represents stained retinae from the contralateral control eye of a chick, wherein the other eye is treated with daily topical administration of a composition comprising 0.3% w/v levodopa; FIG. 13F represents stained retinae from the eye of a chick treated with daily topical administration of a composition comprising 0.3% w/v levodopa; and FIG. 13G represents stained retinae from the eye of an age-matched untreated control chick.

FIG. 14A represents the negative control; FIG. 14B represents the positive control; FIG. 14C represents a retinal section from the eye of an age-matched untreated control chick; FIG. 14D represents a retinal section from the eye of a chick fitted with a translucent diffuser to induce FDM; FIG. 14E represents a retinal section from the eye of a chick treated with daily topical administration of a composition comprising 0.3% w/v levodopa; and FIG. 14F represents a retinal section from the eye of a chick fitted with a translucent diffuser to induce FDM and treated with daily topical administration of a composition comprising 0.3% w/v levodopa.

DETAILED DESCRIPTION OF THE INVENTION

1. Definitions

Figure 1:
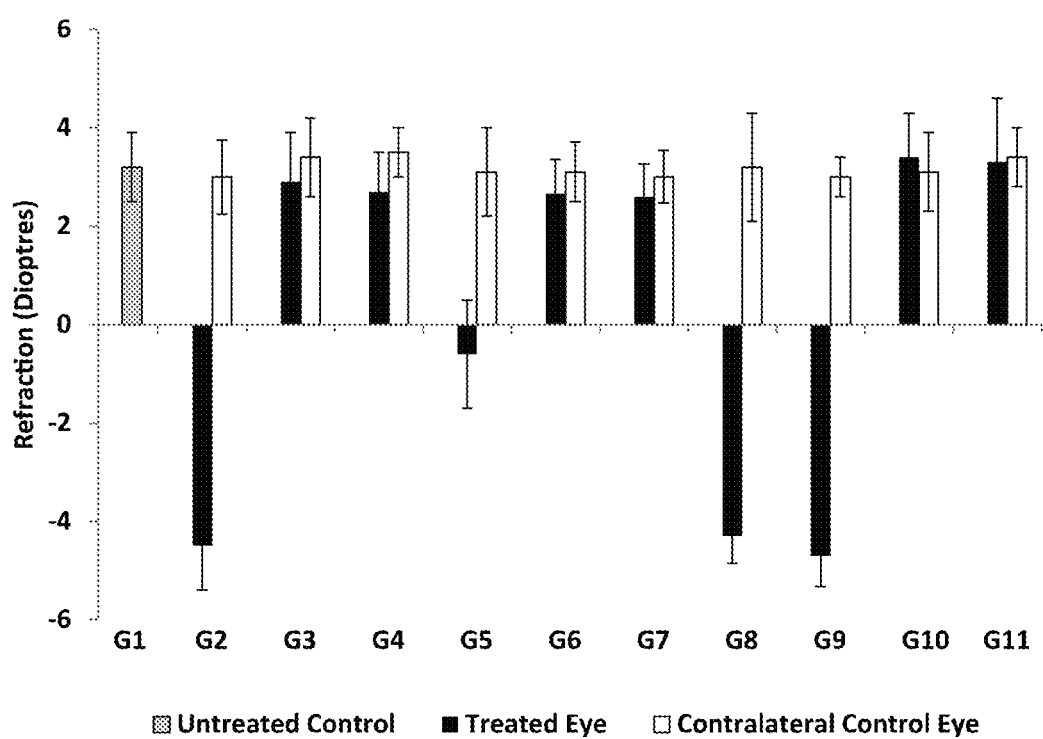
FIG. 1 shows the refractive development in chick eyes in response to diffuser-wear (induction of form deprivation myopia) and treatment with levodopa/carbidopa compositions.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

By "about" is meant a quantity, level, value, number, frequency, percentage, dimension, size, amount, weight or length that varies by as much 15, 14, 13, 12, 11, 10, 9, 8, 7, 6, 5, 4, 3, 2 or 1% to a reference quantity, level, value, number, frequency, percentage, dimension, size, amount, weight or length.

As used herein, the term "and/or" refers to and encompasses any and all possible combinations of one or more of the associated listed items, as well as the lack of combinations when interpreted in the alternative (or).

The phrase "aqueous carrier" is used herein to refer to a liquid aqueous diluent, wherein the aqueous carrier includes, but is not limited to, water, saline, aqueous buffer and aqueous solutions comprising water soluble or water miscible additives such as glucose or glycerol. The aqueous carrier may also be in the form of an oil-in-water emulsion.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. Thus, the use of the term "comprising" and the like indicates that the listed integers are required or mandatory, but that other integers are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

As used herein, the term "condition" refers to an abnormality in the physical state of the body as a whole or one of its parts.

As used herein, the terms "salts" and "prodrugs" include any pharmaceutically acceptable salt, ester, hydrate, solvate or any other compound which, upon administration to the recipient, is capable of providing (directly or indirectly) a desired compound, or an active metabolite or residue thereof. Suitable pharmaceutically acceptable salts include salts of pharmaceutically acceptable inorganic acids such as hydrochloric, sulfuric, phosphoric, nitric, carbonic, boric, sulfamic and hydrobromic acids, or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulfonic, toluenesulfonic, benzenesulfonic, salicylic, sulfanilic, aspartic, glutamic, edetic, stearic, palmitic, oleic, lauric, pantothenic, tannic, ascorbic and valeric acids. Base salts include, but are not limited to, those formed with pharmaceutically acceptable cations, such as sodium, potassium, lithium, calcium, magnesium, ammonium and alkylammonium. Also, basic nitrogen-containing groups may be quaternized with such agents as lower alkyl halides, such as methyl, ethyl, propyl and butyl chlorides, bromides and iodides; dialkyl sulfates such as dimethyl and diethyl sulfate; and others. However, it will be appreciated that non-pharmaceutically acceptable salts also fall within the scope of the invention since these may be useful in the preparation of pharmaceutically acceptable salts. The preparation of salts and prodrugs can be carried out by methods known in the art. For example, metal salts can be prepared by reaction of a desired compound with a metal hydroxide. An acid salt can be prepared by reacting an appropriate acid with a desired compound.

As used herein, the phrase "solubilized form" refers to a form where a compound, such as levodopa, is dissolved in a liquid such that a solution comprising a uniform distribution of the compound is obtained which is substantially free of solid compound. In some embodiments, the liquid is an aqueous carrier as described herein.

The term "subject" as used herein refers to a vertebrate subject, particularly a mammalian or avian subject, for whom therapy or prophylaxis is desired. Suitable subjects include, but are not limited to, primates; avians; livestock animals such as sheep, cows, horses, deer, donkeys and pigs; laboratory test animals such as rabbits, mice, rats, guinea pigs and hamsters; companion animals such as cats and dogs; and captive wild animals such as foxes, deer and dingoes. In particular embodiments, the subject is a human. In some embodiments, the subject is a human child or young adult, for example, from the age of about 2 years to 20 years. However, it will be understood that the aforementioned terms do not imply that symptoms are present.

As used herein, the phrase "visual disorder" refers to a condition that alters the vision of a subject. In particular embodiments, such conditions are associated with a decrease in "visual acuity", which is typically associated with diminishing or lessening of the acuteness or clearness of vision. Thus, a decrease in "visual acuity" typically refers to any measurable diminishing or lessening in the acuteness or clearness of form vision, which is dependent on the sharpness of the retinal focus within the eye and the sensitivity of the interpretative faculty of the brain. In certain embodiments, visual acuity refers to the Snellen acuity (e.g. 20/20).

Each embodiment described herein is to be applied mutatis mutandis to each and every embodiment unless specifically stated otherwise.

2. Compositions

The present invention is based, in part, on the identification that aqueous compositions comprising levodopa and an antioxidant can significantly elevate intraocular dopamine levels. Thus, the inventors conceived that aqueous compositions comprising levodopa and an antioxidant may be useful for inhibiting the development or progression of a visual disorder involving reduced dopamine levels in the eye.

The amount of levodopa in the composition may depend on the visual disorder being treated, the characteristics of the subject such as weight and age, and the route of administration. In some embodiments, the levodopa in the composition is in an amount in the range of from 0.01% to 60% w/v, 0.02% to 50% w/v, 0.03% w/v to 40% w/v, 0.04% to 30% w/v, 0.05% to 20% w/v, 0.06% to 10% w/v, 0.065% to 9% w/v, 0.07% to 8% w/v, 0.075% to 7% w/v, 0.08% to 6% w/v, 0.085% to 5% w/v, 0.09% to 4% w/v, 0.095% to 3% w/v, 0.1% to 2% w/v or 0.105% to 1% w/v of the composition (and all integers therebetween); especially about 0.1%, 0.2%, 0.3%, 0.4%, 0.5%, 0.6%, 0.7%, 0.8%, 0.9% or 1% w/v of the composition.

In preferred embodiments, levodopa is in solubilized form in the composition. A skilled person will be well aware of procedures routinely used in the art to determine the solubility of a compound, for example, the procedures described in Goodwin (2006) *Drug Discovery Today: Technologies*, 3(1): 67-71; Jouyban (2010) Handbook of Solubility Data for Pharmaceuticals (CRC Press); or Hefter and Tomkins (2003) The Experimental Determination of Solubilities (John Wiley & Sons, Ltd). For example, the solubility of a compound may be analyzed using UV spectroscopy or high performance liquid chromatography.

In some embodiments, levodopa may be in the form of a derivative such as a pharmaceutically acceptable salt and/or solvate thereof, or prodrug thereof. In some embodiments, levodopa is in the form of a hydrate. In some embodiments, the pharmaceutically acceptable salt of levodopa is the hydrochloride salt, such as that described in US 2007/0027216 A1. In some embodiments the prodrug of levodopa is (2R)-2-phenylcarbonyloxypropyl(2S)-2-amino-3-(3,4-dihydroxyphenyl)propanoate mesylate as described in US 2009/0156679 A1; or a levodopa ester such as levodopa methyl ester or levodopa ethyl ester, levodopa amide, levodopa carboxamide or levodopa sulfonamide such as those described in US 2014/0088192 A1.

Without wishing to be bound by theory, the use of levodopa, which is naturally synthesized by and present in the human body, is thought to reduce the adverse effects compared with therapy with non-naturally occurring pharmaceutical agents and, thus, the compositions of the invention will be suitable for long-term use. Furthermore, it is thought that the use of a naturally occurring compound will reduce the incidence of tolerance, which has typically developed with existing pharmaceutical agents used for the treatment and/or prevention of visual disorders, such as myopia.

The antioxidant may be any compound that slows down, inhibits or prevents the oxidation of any component of the composition of the invention, especially levodopa. Suitable antioxidants may include, but are not limited to, ascorbic acid or vitamin C, phenolic acids, sorbic acid, sodium bisulfite, sodium metabisulfite, sodium thiosulfate, acetyl cysteine, sodium thiosulfate, ethylene diamine tetraacetic acid (EDTA), sodium nitrite, ascorbyl stearate, ascorbyl palmitate, alpha-thioglycerol, erythorbic acid, cysteine hydrochloride, citric acid, tocopherol or vitamin E, tocopherol acetate, dibutylhydroxytoluene, soybean lecithin, sodium thioglycolate, butylhydroxyanisole, propyl gallate, uric acid, melatonin, thiourea, or salts or combinations thereof. In some embodiments, the antioxidant is ascorbic acid or a salt thereof.

The antioxidant may be present in an amount suitable to substantially slow down, inhibit or prevent oxidation of any component of the composition of the invention, especially levodopa. For example, the antioxidant may be present in an amount in the range of from 0.01% to 10% w/v, 0.01% to 5% w/v, 0.03% to 4% w/v, 0.05% to 3% w/v, 0.07% to 2% w/v, 0.09% to 1% w/v or 0.1% to 0.5% w/v of the composition; especially in an amount of about 0.1% w/v of the composition.

The aqueous carrier is preferably a pharmaceutically acceptable aqueous carrier. A variety of pharmaceutically acceptable aqueous carriers well known in the art may be used. For example, the aqueous carrier may be selected from, but is not limited to, saline, water, aqueous buffer, an aqueous solution comprising water and a miscible solvent, and combinations thereof. In some embodiments, the aqueous carrier is saline. When saline is used, it is preferably isotonic for the point of administration, such as the eye. For example, in some embodiments the saline comprises 0.15 to 8% w/v sodium chloride; especially 0.18% to 7% w/v, 0.22% to 5% w/v or 0.45% to 3% w/v sodium chloride; more especially 0.5 to 2% w/v or 0.65% to 1.5% w/v sodium chloride; most especially about 0.9% w/v sodium chloride.

In some embodiments where the aqueous carrier is not isotonic, for example water, the composition may contain a tonicity agent. Any pharmaceutically acceptable tonicity agent well known in the art may be used. Suitable tonicity agents include, but are not limited to, boric acid, sodium acid phosphate buffer, sodium chloride, glucose, trehalose, potassium chloride, calcium chloride, magnesium chloride, polypropylene glycol, glycerol, mannitol, or salts or combinations thereof. The tonicity agent may be present in the composition in an amount that provides isotonicity with the point of administration, such as the eye, for example in the range of from 0.02 to 15% w/v.

In some embodiments the aqueous carrier is a buffer, wherein the buffer maintains a pH in the range of from 5 to 8, 5.2 to 7.4, 5.5 to 7.4 or 5.5 to 6. In some embodiments, the buffer maintains a pH in the range of from 5.5 to 6.5, especially 5.5 to 6 or 6 to 6.5. Suitable buffering agents include, but are not limited to, acetic acid, citric acid, sodium metabisulfite, histidine, sodium bicarbonate, sodium hydroxide, boric acid, borax, alkali metal phosphates, phosphate or citrate buffers, or combinations thereof. The buffering agent may be present in the composition in an amount suitable to maintain the desired pH.

In some embodiments, the pH of the composition is in the range of from 5 to 8, 5.2 to 7.4, 5.5 to 7.4 or 5.5 to 6. In some embodiments, the pH of the composition is in the range of from 5.5 to 6.5, especially 5.5 to 6 or 6 to 6.5. In some embodiments, the pH of the composition is in the range of from 5.5 to 6. In some embodiments, the pH of the composition is in the range of from 6 to 6.5.

In some embodiments, the composition of the invention further comprises an inhibitor of aromatic L-amino acid decarboxylase. Suitable inhibitors of aromatic L-amino acid decarboxylase include, but are not limited to, carbidopa, benserazide, methyldopa, or salts or combinations thereof. In some embodiments, the inhibitor of aromatic L-amino acid decarboxylase is carbidopa. Without wishing to be bound by theory, the inhibitor of aromatic L-amino acid decarboxylase is thought to reduce the conversion of levodopa to dopamine within non-neuronal tissue and, accordingly, increase the bioavailability of levodopa in the composition of the invention.

The amount of the inhibitor of aromatic L-amino acid decarboxylase in the composition of the invention will depend on the condition being treated, the route of administration of the composition and the amount of levodopa in the composition. The inhibitor of aromatic L-amino acid decarboxylase should be present in an amount sufficient to substantially inhibit the decarboxylation of levodopa. In some embodiments, the ratio of levodopa to the inhibitor of aromatic L-amino acid decarboxylase is in the range of from 20:1 to 1:1, 15:1 to 1:1, 10:1 to 1:1, 9:1 to 1:1, 8:1 to 1:1, 7:1 to 1:1, 6:1 to 2:1 or 5:1 to 3:1. In some embodiments, the ratio of levodopa to the inhibitor of aromatic L-amino acid decarboxylase is about 4:1.

In some embodiments, the inhibitor of aromatic L-amino acid decarboxylase in the composition is in an amount in the range of from 0.0005% to 30% w/v, 0.0025% to 15% w/v, 0.005% to 12.5% w/v, 0.0075% to 10% w/v, 0.01% to 7.5% w/v, 0.0125% to 5% w/v, 0.015% to 2.5% w/v, 0.0163% to 2.25% w/v, 0.0175% to 2% w/v, 0.0188% to 1.75% w/v, 0.02% to 1.5% w/v, 0.0213% to 1.25% w/v, 0.0225% to 1% w/v, 0.0238% to 0.75% w/v, 0.025% to 0.5% w/v, 0.0263% to 0.25% w/v of the composition (and all integers therebetween); especially about 0.025%, 0.03%, 0.035%, 0.04%, 0.045%, 0.05%, 0.055%, 0.06%, 0.065%, 0.07%, 0.075%, 0.08%, 0.085%, 0.09%, 0.095%, 0.1%, 0.125%, 0.15%, 0.175%, 0.2%, 0.225% or 0.25% w/v of the composition.

The composition may also comprise or may be administered separately, simultaneously or sequentially with one or more ancillary pharmaceutically active agents. In some embodiments, the ancillary pharmaceutically active agent may increase activation of the dopaminergic system. Exemplary ancillary pharmaceutically active agents include, but are not limited to, a dopamine receptor agonist, a gamma-aminobutyric acid (GABA) receptor antagonist and/or a muscarinic acetylcholine receptor antagonist. In some embodiments, the pharmaceutically active agent is an agent that is used for inhibiting the development or progression of a visual disorder, particularly a visual disorder involving reduced dopamine levels in the eye, such as myopia.

Without wishing to be bound by theory, it is thought that the administration of more than one pharmaceutically active agent may reduce the development of tolerance to therapy with one pharmaceutically active agent alone, particularly when the pharmaceutically active agents have differing mechanisms of action and/or different molecular targets. For example, the administration of the composition of the invention with an existing pharmaceutical treatment for a visual disorder, such as atropine, may reduce the occurrence of receptor desensitization in response to the existing pharmaceutical treatment. It is also thought that the administration of more than one pharmaceutically active agent may result in a greater therapeutic effect than administration of each agent alone, such as increased efficacy, decreased adverse effects and/or decreased tolerance.

In some embodiments, the composition of the invention further comprises a dopamine receptor agonist. The dopamine receptor agonist may have agonist activity at any dopamine receptor subtype, including, but not limited to, any receptor subtype from the $D_1$-like ($D_1$ and $D_5$ receptors) and $D_2$-like ($D_2$, $D_3$ and $D_4$ receptors) families of receptors, and dopamine receptor heterodimers. Suitable dopamine receptor agonists include, but are not limited to, quinpirole, apomorphine, ropinirole, pramipexole, dexpramipexole, piribedil, rotigotine, bromocriptine, lisuride, cabergoline, 2-amino-6,7-dihydroxy-1,2,3,4-tetrahydronaphthalene (ADTN), pergolide, calidopa, dihydrexidine, doxathrine, propylnorapomorphine, quinagolide, roxindole, sumanirole, fenoldopam, ergocornine, 1-phenyl-2,3,4,5-tetrahydro-(1H)-3-benzazepine-7,8-diol (also known as SKF-38393), 2-(N-phenethyl-N-propyl)amino-5-hydroxytetralin (PPHT; also known as N-0434), dihydroergotamine, (1R,3S)-1-(aminomethyl)-3-phenyl-3,4-dihydro-1H-isochromene-5,6-diol (also known as A-68930), carmoxirole, fenoldopam, or salts or combinations thereof. In some embodiments, the dopamine receptor agonist is dihydroergotamine tartrate, 2-(N-phenethyl-N-propyl)amino-5-hydroxytetralin hydrochloride or (1R,3S)-1-(aminomethyl)-3-phenyl-3,4-dihydro-1H-isochromene-5,6-diol hydrochloride. In some embodiments, the dopamine receptor agonist is selected from ADTN, quinpirole, apomorphine, and salts and combinations thereof; especially ADTN and salts thereof.

The amount of dopamine receptor agonist in the composition may depend on the condition being treated and the route of administration. In some embodiments, the dopamine receptor agonist in the composition is in an amount in the range of from 0.01% to 20% w/v, 0.01% to 10% w/v, 0.01% to 5% w/v, 0.03% to 3% w/v, 0.033% to 2.7% w/v, 0.038% to 2.4% w/v, 0.043% to 2.1% w/v, 0.05% to 1.8% w/v, 0.06% to 1.5% w/v, 0.075% to 1.2% w/v, 0.1% to 0.9% w/v or 0.15 to 0.6% w/v of the composition (and all integers therebetween); especially about 0.2%, 0.21%, 0.22%, 0.23%, 0.24%, 0.25%, 0.26%, 0.27%, 0.28%, 0.29%, 0.3%, 0.31%, 0.32%, 0.33%, 0.34%, 0.35%, 0.36%, 0.37%, 0.38%, 0.39%, or 0.4% w/v of the composition.

In some embodiments, the composition of the invention further comprises a GABA receptor antagonist. The GABA receptor antagonist may have antagonist activity at any GABA receptor subtype, including, but not limited to, GABAA, GABAB and/or GABAA-rho (formerly GABAc) receptors. Suitable GABA receptor antagonists include, but are not limited to, bicuculline, flumazenil, gabazine, phenylenetetrazol, (1,2,5,6-tetrahydropyridin-4-yl)methylphosphinic acid (TPMPA), (3-aminopropyl)(cyclohexylmethyl) phosphinic acid (also known as CGP-46381), 4-imidazoleacetic acid, picrotoxin, piperidin-4-ylphosphinic acid (PPA), piperidin-4-ylseleninic acid (SEPI), 3-aminopropyl-N-butylphosphinic acid (also known as CGP-36742), (piperidin-4-yl)methylphosphinic acid (P4MPA), or salts or combinations thereof.

In some embodiments, the GABA receptor antagonist is selected from TPMPA, bicuculline and salts and combinations thereof.

The amount of GABA receptor antagonist in the composition may depend on the condition being treated and the route of administration. In some embodiments, the GABA receptor antagonist in the composition is in an amount in the range of from 0.01% to 20% w/v, 0.01% to 10% w/v, 0.01% to 5% w/v, 0.03% to 3% w/v, 0.033% to 2.7% w/v, 0.038% to 2.4% w/v, 0.043% to 2.1% w/v, 0.05% to 1.8% w/v, 0.06% to 1.5% w/v, 0.075% to 1.2% w/v, 0.1% to 0.9% w/v or 0.15 to 0.6% w/v of the composition (and all integers therebetween); especially about 0.2%, 0.21%, 0.22%, 0.23%, 0.24%, 0.25%, 0.26%, 0.27%, 0.28%, 0.29%, 0.3%, 0.31%, 0.32%, 0.33%, 0.34%, 0.35%, 0.36%, 0.37%, 0.38%, 0.39%, or 0.4% w/v of the composition.

In some embodiments, the composition of the invention further comprises a muscarinic acetylcholine receptor antagonist. The muscarinic acetylcholine receptor antagonist may have antagonist activity at any muscarinic acetylcholine receptor subtype, including, but not limited to, $M_1$, $M_2$, $M_3$, $M_4$ and $M_5$ receptors. Suitable muscarinic receptor antagonists include, but are not limited to, atropine, pirenzepine, himbacine, hyoscine, cyclopentolate, ipratropium, oxitropium, tropicamide, oxybutynin, tolterodine, diphenhydramine, dicycloverine, flavoxate, tiotropium, trihexyphenidyl, solifenacin, darifenacin, benzatropine, mebeverine, procyclidine, aclidinium, muscarinic toxin 1 (MT1), muscarinic toxin 2 (MT2), muscarinic toxin 3 (MT3), muscarinic toxin 4 (MT4), muscarinic toxin 7 (MT7), or salts or combinations thereof. In some embodiments, the muscarinic acetylcholine receptor antagonist is selected from atropine, pirenzepine, himbacine, and salts and combinations thereof; especially atropine and pirenzepine and salts and combinations thereof.

The amount of muscarinic acetylcholine receptor antagonist in the composition may depend on the condition being treated and the route of administration. In some embodiments, the muscarinic acetylcholine receptor antagonist in the composition is in an amount in the range of from 0.01% to 30% w/v, 0.2% to 20% w/v, 0.22% to 18% w/v, 0.25% to 16% w/v, 0.29% to 14% w/v, 0.33% to 12% w/v, 0.4% to 10% w/v, 0.5% to 8% w/v, 0.67% to 6% w/v or 1% to 4% w/v of the composition (and all integers therebetween); especially about 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9% or 4% w/v of the composition. In particular embodiments, the muscarinic acetylcholine receptor antagonist in the composition is in an amount in the range of from 0.0001% to 30% w/v, 0.0003% to 20% w/v, 0.0005% to 10% w/v, 0.0007% to 5% w/v, 0.0009% to 2% w/v, 0.001% to 1% w/v, 0.003% to 0.5%, 0.005% to 0.2%, 0.007% to 0.15% w/v, or 0.009% to 0.1% of the composition (and all integers therebetween); especially about 0.001%, 0.002%, 0.003%, 0.004%, 0.005%, 0.006%, 0.007%, 0.008%, 0.009%, 0.01%, 0.011%, 0.012%, 0.013%, 0.014%, 0.015%, 0.016%, 0.017%, 0.018%, 0.019% or 0.02% w/v of the composition; most especially about 0.01% w/v of the composition.

The composition of the invention may further comprise a surfactant. A variety of pharmaceutically acceptable surfactants well known in the art may be used. Exemplary surfactants include, but are not limited to, surfactants of the following classes: alcohols; amine oxides; block polymers; carboxylated alcohol or alkylphenol ethoxylates; carboxylic acids/fatty acids; ethoxylated arylphenols; ethoxylated fatty esters, oils, fatty amines or fatty alcohols such as cetyl alcohol; fatty esters; fatty acid methyl ester ethoxylates; glycerol esters such as glycerol monostearate; glycol esters; lanolin-based derivatives; lecithin or derivatives thereof; lignin or derivatives thereof; methyl esters; monoglycerides or derivatives thereof; polyethylene glycols; polypropylene glycols; alkylphenol polyethylene glycols; alkyl mercaptan polyethylene glycols; polypropylene glycol ethoxylates; polyethylene glycol ethers such as Cetomacrogol 1000; polymeric surfactants; propoxylated and/or ethoxylated fatty acids, alcohols or alkylphenols; protein-based surfactants; sarcosine derivatives; sorbitan derivatives such as polysorbates; sorbitol esters; esters of sorbitol polyglycol ethers; fatty acid alkylolamides; N-alkylpolyhydroxy fatty acid amide; N-alkoxypolyhydroxy fatty acid amide; alkyl polyglycosides; quaternary ammonium compounds such as benzalkonium chloride; cyclodextrins such as alpha-, beta- or gamma-cyclodextrin; sucrose or glucose esters or derivatives thereof; sulfosuccinates such as dioctyl sodium sulfosuccinate; or combinations thereof. Without wishing to be bound by theory, the presence of a surfactant may be useful in emulsifying the aqueous carrier with an oil if an oil is included in the composition and may enhance the penetration of the active ingredients, such as levodopa, through the corneal epithelium. The surfactant may be present in an amount in the range of from about 0.1% to 30% w/v of the composition.

In some embodiments, the composition of the invention further comprises a rheology modifier. The rheology modifier may be used to alter the surface tension and flow of the composition and may also contribute to the composition's residence time on the surface of the eye when formulated for topical administration. Suitable rheology modifiers are well known in the art. For example, the rheology modifier may be selected from, but is not limited to, hyaluronic acid, chitosan, polyvinyl alcohol, polyethylene glycol, polyvinyl pyrrolidone, dextran, methylcellulose, hydroxypropylmethylcellulose, hydroxyethylcellulose, hydroxypropylcellulose, hydroxypropyl guar, acrylates such as Carbopol polymers, poloxamers, gum arabic, xanthan gum, guar gum, locust bean gum, carboxymethylcellulose, alginate, starch (from rice, corn, potato or wheat), carrageenan, konjac, aloe vera gel, agarose, pectin, tragacanth, curdlan gum, gellan gum, scleroglucan, and derivatives and combinations thereof. The rheology modifier should be present in an amount sufficient to obtain the desired viscosity of the composition. The rheology modifier may be present in an amount in the range of from about 0.5% to 5% w/v of the composition.

The composition of the invention may further comprise a preservative. The preservative may be particularly useful for preventing microbial contamination in a composition which is subject to multiple uses from the same container, for example, if the composition of the invention is formulated for topical administration in a multiple unit dose form. Suitable preservatives include any pharmaceutically acceptable preservative routinely used in the art to prevent microbial contamination in a composition. Non-limiting examples include sodium perborate, stabilized oxychloro complex, polyquaternium-1, phenylmercuric acid, benzalkonium chloride, chlorbutanol, phenylmercuric acetate, phenylmercuric nitrate, chlorhexidine, benzododecinium bromide, cetrimonium chloride, thiomersal, methyl parahydroxybenzoate, propyl parahydroxybenzoate, polyquaternium ammonium chloride, polyaminopropyl biguanide, hydrogen peroxide, benzoic acid, phenolic acids, sorbic acid, benzyl alcohol or salts or combinations thereof. The preservative should be present in an amount that provides adequate preservative activity. For example, the preservative may be present in an amount in the range of from about 0.001% to 1% w/v of the composition.

It may be desirable to increase the permeation of the composition into the eye. This may be particularly useful when the composition is formulated for topical administration. Accordingly, the composition of the invention may also comprise a permeation enhancing agent. In this regard, the composition of the invention may comprise, but is not limited to, dimethyl sulfoxide (DMSO); cyclodextrins such as alpha-, beta- or gamma-cyclodextrin; EDTA; decamethonium; glycocholate; cholate; saponins; fusidate; taurocholates; polyethylene glycol ethers; polysorbates; or salts, derivatives or combinations thereof. In some embodiments, the permeation enhancing agent is dimethyl sulfoxide. Other permeation enhancing agents include nanoparticles, liposomes or micelles which, in some embodiments, encapsulate levodopa. The permeation enhancing agent should be present in an amount that facilitates permeation of levodopa across the corneal epithelium. For example, the permeation enhancing agent may be present in an amount in the range of from about 0.1% to 30% w/v of the composition.

In particular embodiments, the permeation enhancing agent is a micelle. Suitable micelles include, but are not limited to, a Triton X-100 micelle e.g. the micelle described in Jodko-Piorecka and Litwinienko (2015) *Free Radical Biology and Medicine*, 83: 1-11; a surfactant nanomicelle e.g. a nanomicelle formed with sodium dodecyl sulfate, dodecyltrimethylammonium bromide, n-dodecyl tetra (ethylene oxide), Vitamin E TGPS, octoxynol-40 and/or dioctanoyl phosphatidylcholine; a polymeric micelle e.g. a micelle formed with poly(caprolactone), poly (D,L-lactide), polypropylene oxide, poly(β-benzyl-1-aspartate), methoxy poly(ethylene glycol)-hexylsubstituted poly(lactide), Pluronic F127 poly(oxyethylene)/poly(oxypropylene)/poly(oxyethylene), F 68, F 127, poly(hydroxyethylaspartamide)-polyethylene glycol-hexadecylamine, polyoxyl 40 stearate, N-isopropylacrylamide with vinyl pyrrolidone and acrylic acid cross-linked with N,N'-methylene bis-acrylamide, Pluronic F127 and chitosan, poly(lactic acid), poly(glycolic acid), poly(ethylene glycol), poly(ethylene oxide), N-phthaloylcarboxymethylchitosan, poly(2-ethylhexyl acrylate)-b-poly(acrylic acid), poly(tert-butyl acrylate)-b-poly(2-vinylpyridine), poly(ethylene oxide)-b-polycaprolactone, poly (ε-caprolactone)-b-poly(ethylene glycol)-b-poly(ε-caprolactone), poly(ε-caprolactone)-b-poly(methacrylic acid), poly(ethyleneglycol)-b-poly(ε-caprolactone-co-trimethylenecarbonate), poly(aspartic acid)-b-polylactide, poly(ethylene glycol)-block-poly(aspartate-hydrazide), poly(N-isopropylacrylamide-co-methacrylic acid)-g-poly(D,L-lactide) and/or stearic acid-grafted chitosan oligosaccharide; or the micelles disclosed in US 2009/0092665 A1. In particular embodiments, the micelle encapsulates the levodopa in the composition.

The composition of the invention may also further comprise a chelating agent. Suitable chelating agents include, but are not limited to, amino carboxylic acids or salts thereof such as EDTA, nitrilotriacetic acid, nitrilotripropionic acid, diethylenetriamine pentacetic acid, 2-hydroxyethyl-ethylenediamine-triacetic acid, 1,6-diamino-hexamethylene-tetraacetic acid, 1,2-diamino-cyclohexane tetraacetic acid, 0,0'-bis(2-aminoethyl)-ethyleneglycol-tetraacetic acid, 1,3-diaminopropane-tetraacetic acid, N,N-bis(2-hydroxybenzyl) ethylenediamine-N,N-diacetic acid, ethylenediamine-N,N'-diacetic acid, ethylenediamine-N,N'-dipropionic acid, triethylenetetraamine hexaacetic acid, 7,19,30-trioxa-1,4,10, 13,16,22,27,33-octaazabicyclo[11,11,11]pentatriacontane (O-bis-tren), ethylenediamine-N,N'-bis(methylenephosphonic acid), iminodiacetic acid, N,N-bis(2-hydroxyethyl)glycine (DHEG), 1,3-diamino-2-hydroxypropane-tetraacetic acid, 1,2-diaminopropane-tetraacetic acid, ethylenediamine-tetrakis(methylenephosphonic acid), N-(2-hydroxyethyl) iminodiacetic acid, or combinations or salts thereof; especially pharmaceutically acceptable salts or mixed salts of EDTA, such as disodium, trisodium, tetrasodium, dipotassium, tripotassium, lithium, dilithium, ammonium, diammonium, calcium or calcium-disodium; most especially disodium EDTA. The chelating agent may be present in an amount in the range of from about 0.01% to 1% w/v of the composition.

In some embodiments, the composition of the invention may further comprise an oil. Suitable oils include, but are not limited to, almond oil; castor oil; mineral oil; olive oil; peanut oil; coconut oil; soybean oil; corn oil; anise oil; clove oil; cassia oil; cinnamon oil; arachis oil; maize oil; caraway oil; rosemary oil; peppermint oil; eucalyptus oil; seed oils such as canola oil, cottonseed oil, linseed oil, safflower oil, sesame oil or sunflower oil; silicone oil; or combinations thereof. Such oils may be included in the composition in the form of an oil-in-water emulsion, optionally with a surfactant, with the aqueous carrier. The oil may be present in an amount in the range of from about 0.1% to 20% w/v of the composition.

The composition of the invention may further comprise any other pharmaceutically acceptable excipient commonly present in ocular formulations. For example, the compositions may further comprise an alcohol such as isopropanol, benzyl alcohol, cetearyl alcohol or ethanol; a lubricant such as glucose, glycerol, polyethylene glycol, polypropylene glycol or derivatives thereof; a polysaccharide such as chitosan, chitin, dermatan, hyaluronate, heparin, dermatan, chondroitin, cyclodextrin or derivatives thereof; or combinations thereof. Suitable pharmaceutically acceptable carriers include, but are not limited to, aqueous carriers as described herein, oils as described herein, fatty acids, a silicone liquid carrier such as a perfluorocarbon or fluorinated liquid carrier, for example, as described in U.S. Pat. No. 6,458,376 B1, and combinations thereof. In some embodiments, the composition does not comprise an antioxidant.

In particular embodiments, the composition of the invention may be formulated for topical administration to the eye. In this regard, the composition of the invention may be in the form of an eye drop or gel; especially an eye drop. Without wishing to be bound by theory, formulating the composition for topical administration to the eye is thought to increase user compliance, particularly when the composition is used as a preventative or control measure. This may be particularly important if the composition is administered to a child subject. Furthermore, such a formulation may reduce the incidence of off target effects of levodopa.

In some embodiments, the composition of the invention is formulated for penetration of levodopa through the corneal epithelium. In preferred embodiments, greater than about 10%, 20%, 30%, 40%, 50%, 60%, 70% or 80% of the dose of levodopa penetrates the corneal epithelium.

When formulated as an eye drop or gel, the composition of the invention may be in a single unit dose or multiple unit dose form, preferably a multiple unit dose form.

In alternative embodiments, the composition of the invention is formulated for direct injection into the eye. In particular embodiments, the composition of the invention is formulated for intravitreal, subconjunctival, intracameral, intrascleral, intracorneal or subretinal injection; especially intravitreal, intrascleral or intracorneal injection. In some embodiments, the composition of the invention is formulated for suprachoroidal injection. In some embodiments, the composition of the invention is formulated for injection via a microneedle, for example, via intrascleral or intracorneal administration.

Other excipients and components of the composition may be readily determined by a person skilled in the art. Techniques for formulation and administration may be found in, for example, Remington (1980) Remington's Pharmaceutical Sciences, Mack Publishing Co., Easton, Pa., latest edition; and suitable excipients may be found in, for example, Katdare and Chaubel (2006) Excipient Development for Pharmaceutical, Biotechnology and Drug Delivery Systems (CRC Press).

A person skilled in the art would be familiar with the components of the compositions of the invention and, accordingly, would readily be able to synthesize or source the components, such as from, for example, Sigma Aldrich Co. LLC. For example, levodopa is commercially available from a number of sources, such as Sigma-Aldrich Co. LLC, and a synthetic route is available in, for example, Vandanyan and Hruby (2006) Synthesis of Essential Drugs (Elsevier) pages 136-137; Vandanyan and Hruby (2016) Synthesis of Best-Seller Drugs (Academic Press) pages 180-182; and U.S. Pat. No. 4,962,223; all of which are incorporated herein by reference in their entirety.

3. Processes for Preparing the Composition

The inventors have found that the composition of the invention may be prepared by dissolving levodopa in the aqueous carrier at a pH in the range of from 0.5 to 2.5, adding the antioxidant to the composition and adjusting the pH of the composition to a pH in the range of from 5 to 8.

The pH at which levodopa is dissolved in the aqueous carrier is in the range of from 0.5 to 2.5, preferably 1 to 2, most especially 1.5 to 2. In some embodiments, levodopa is dissolved in the aqueous carrier at a pH of about 2. Without wishing to be bound by theory, the maintenance of the aqueous carrier at an acidic pH is thought to increase the solubility of levodopa in the aqueous carrier.

The pH of the final composition is in the range of from 5 to 8, preferably 5.5 to 7.5, especially 5.5 to 7.4, most especially 5.5 to 6. In some embodiments, the pH of the composition is in the range of from 5.5 to 6.5, especially 5.5 to 6 or 6 to 6.5. In some embodiments, the pH of the composition is adjusted to a pH in the range of from 5.5 to 6. In some embodiments, the pH of the composition is adjusted to a pH in the range of from 6 to 6.5.

The pH of the compositions may be adjusted using any pharmaceutically acceptable pH adjusting agent that is routinely used in the art, such as hydrochloric acid, sodium hydroxide, etc. A person skilled in the art will be well aware of suitable agents.

The inhibitor of aromatic L-amino acid decarboxylase, excipients and other components of the composition of the invention may be added to the composition at any stage of the process. For example, the inhibitor of aromatic L-amino acid decarboxylase may be added to the solution of levodopa and aqueous carrier at a pH in the range of from 0.5 to 2.5 prior to adjusting the pH of the composition to a pH in the range of from 5 to 8, or may be added to the composition after adjusting the pH of the composition to a pH in the range of from 5 to 8. In some embodiments, the inhibitor of aromatic L-amino acid decarboxylase and levodopa are simultaneously dissolved in the aqueous carrier at a pH in the range of from 0.5 to 2.5.

The composition of the invention may also be sterilized prior to use, for example by filtration, autoclaving and/or gamma irradiation.

Without wishing to be bound by theory, the preparation of the composition of the invention using this process increases the solubility of levodopa in the aqueous carrier, thereby removing the need for the presence of organic carriers or agents which enhance the solubility of levodopa in the composition.

4. Methods of Prevention and Treatment of a Visual Disorder

The compositions of the invention are useful for inhibiting the progression or development of a visual disorder in a subject, particularly a visual disorder involving reduced dopamine levels in the eye, such as a visual disorder associated with diabetic retinopathy or Parkinson's disease, or myopia. Accordingly, the compositions of the invention may be used in methods of inhibiting the progression or development of a visual disorder in a subject. The compositions of the invention may also be used in the manufacture of a medicament for the uses described herein.

The compositions of the invention are useful for inhibiting the progression of a visual disorder in a subject. In this regard, the compositions of the invention may be used for treating a visual disorder. In some embodiments, the compositions of the invention may slow the progression of a visual disorder in a subject.

The compositions of the invention are also useful for inhibiting the development of a visual disorder in a subject. Thus, the compositions of the invention are useful for preventing a visual disorder in a subject. In some embodiments, the compositions of the invention may delay the onset of a visual disorder in a subject, i.e. may increase the age of the subject at which the visual disorder is developed and, therefore, the possible severity of the visual disorder.

The visual disorder may be any visual disorder involving reduced dopamine levels in the eye, particularly reduced dopamine levels in the retina. Accordingly, the visual disorder may be any visual disorder where increasing dopamine levels in the eye, particularly the retina, is associated with effective inhibition of the progression or development of the visual disorder.

There are numerous visual disorders involving reduced dopamine levels in the eye. For example, the visual disorder may be, but is not limited to, a visual disorder associated with diabetic retinopathy or Parkinson's disease, myopia, increased ocular growth, reduced spatial and temporal contrast sensitivity, amblyopia, blurred or double vision, eye strain, trouble with voluntarily opening the eyes (apraxia), eyelid spasms (blepharospasm), excessive blinking, altered color perception, reduced depth perception or visual hallucinations. In some embodiments, the visual disorder is selected from a visual disorder associated with diabetic retinopathy or Parkinson's disease, and myopia. In particular embodiments, the visual disorder is myopia.

In some embodiments, the visual disorder is not associated with Parkinson's disease.

The method includes administering the composition of the invention to a subject. The composition of the invention may be administered locally through topical administration to the surface of the eye or via direct injection into the eye.

In some embodiments, the composition is topically administered to the eye, for example, in the form of an eye drop or gel. In preferred embodiments, the composition is applied as an eye drop. The composition of the invention may be applied to any surface of the eye, preferably the cornea/sclera, thereby allowing the components present in the composition, particularly levodopa, to penetrate into the eye. In some embodiments, the composition is formulated such that levodopa penetrates through the corneal epithelium.

In other embodiments, the composition is administered by injection into the eye. For example, the composition may be injected directly into the sclera, anterior chamber or vitreous, or may be injected into the subconjunctival, peribulbar, retrobulbar or suprachoroidal space. In particular embodiments, the composition of the invention is administered via intravitreal, subconjunctival, intracameral, intrascleral, intracorneal or subretinal injection; especially intravitreal, intrascleral or intracorneal injection. In some embodiments, the composition of the invention is administered via suprachoroidal injection. In some embodiments, the composition of the invention is administered by intravitreal injection. In other embodiments, the composition of the invention is injected using a microneedle, for example, via intrascleral or intracorneal administration. For administration via these routes, the composition of the invention may be in the form of a sterile injectable solution.

The portion of the eye into or onto which the composition of the invention is preferably administered is the portion that allows for penetration of the components, particularly levodopa, into the eye, preferably into the retina. Administration is preferably performed on the cornea/sclera and conjunctiva for topical administration, or the composition may be injected into the subconjunctival, peribulbar, retrobulbar or suprachoroidal space, or into the sclera, cornea, anterior chamber or vitreous.

When applied topically, the composition of the invention may be used with both hard and soft contact lenses.

Dosage regimens may be established for different indications in accordance with methodologies well known to a person skilled in the art. The dosage of the composition will depend on the condition to be treated, the age of the subject and the route of administration.

The composition of the invention may be administered topically or by injection in a suitable amount so as to provide a dose of levodopa in the range of from 0.001 mg/kg/day to 12 mg/kg/day, especially from 0.001 mg/kg/day to 4 mg/kg/day, more especially from 0.001 mg/kg/day to 2 mg/kg/day. In some embodiments the composition is administered in a suitable amount so as to provide a dose of levodopa in the range of from 0.001 mg/kg/day to 30 mg/kg/day, especially from 0.001 mg/kg/day to 12 mg/kg/day, more especially from 0.001 mg/kg/day to 4 mg/kg/day, most especially from 0.001 mg/kg/day to 2 mg/kg/day When administered topically as an eye drop, the composition of the invention may be administered in an amount in the range of from 1 to 6 drops per eye (and all integers therebetween), which may equate to, for example, an amount in the range of from about 0.04 mL to 0.24 mL per eye (and all integers therebetween). Drops may be applied to each eye from 1 to 4 times daily. When the composition of the invention is formulated as a gel, an equivalent dose is provided. A skilled person will be aware of suitable dispensers for topical application of the composition of the invention.

When administered by injection, the composition of the invention may be administered in an amount in the range of from 0.001 mL to 0.5 mL (and all integers therebetween), especially about 0.01 mL. The composition of the invention may be administered at a frequency of once per week to once daily.

In order that the invention may be readily understood and put into practical effect, particular preferred embodiments will now be described by way of the following non-limiting examples.

EXAMPLES

All materials used in the following examples are commercially available from, for example, Sigma-Aldrich Co. LLC unless otherwise indicated.

Example 1—Method of Producing 0.3% W/V Levodopa Composition 12 mg levodopa (commercially available from Sigma-Aldrich Co. LLC) was dissolved in a solution containing 0.15 M hydrochloric acid, 0.1% ascorbic acid and 1× phosphate buffered saline (PBS) (solution is approximately pH 2). Once levodopa was dissolved, the solution was adjusted to a pH of 6 using sodium hydroxide to obtain a final volume of 4 mL.

Example 2—Method of Producing 0.3% W/V Levodopa, 0.08% W/V Carbidopa Composition 12 mg levodopa was dissolved in a solution containing 0.15 M hydrochloric acid, 0.1% ascorbic acid and 1×PBS (solution is approximately pH 2). Once levodopa was dissolved, 3 mg of carbidopa (commercially available from Sigma-Aldrich Co. LLC) was added to the solution. The solution was adjusted to a pH of 6 using sodium hydroxide to obtain a final volume of 4 mL.

Example 3—Method of Producing 0.03% W/V Levodopa, 0.008% W/V Carbidopa Composition 1.2 mg levodopa was dissolved in a solution containing 0.15 M hydrochloric acid, 0.1% ascorbic acid and 1×PBS (solution is approximately pH 2). Once levodopa was dissolved, 0.3 mg of carbidopa was added to the solution. The solution was adjusted to a pH of 6 using sodium hydroxide to obtain a final volume of 4 mL.

Example 4—Efficacy of Levodopa Compositions in Preventing Form Deprivation Myopia 44 male White Cockerel chickens were randomly assigned to one of 11 treatment groups as defined below (n=4 per group) and were treated for a five day period. G1-G11 represent the labelling system used in FIGS. 1 and 2.

G1. Age-matched untreated control group
G2. Chicks fitted with a translucent diffuser over their left eye to induce form-deprivation myopia (FDM)
G3. Chicks fitted with a translucent diffuser over their left eye and daily intravitreal injection of the composition of Example 2
G4. Chicks fitted with a translucent diffuser over their left eye and daily topical administration of the composition of Example 2
G5. Chicks fitted with a translucent diffuser over their left eye and daily oral administration of 10 mg/kg levodopa, 2.5 mg/kg carbidopa as a powder
G6. Chicks fitted with a translucent diffuser over their left eye and daily intravitreal injection of the composition of Example 3
G7. Chicks fitted with a translucent diffuser over their left eye and daily topical administration of the composition of Example 3
G8. Chicks fitted with a translucent diffuser over their left eye and daily intravitreal injection of a vehicle solution (buffered 0.1% ascorbic acid in 1×PBS)
G9. Chicks fitted with a translucent diffuser over their left eye and daily topical administration of a vehicle solution (buffered 0.1% ascorbic acid in 1×PBS)
G10. Daily intravitreal injection of the composition of Example 2
G11. Daily topical administration of the composition of Example 2

For the drug treatments, the compositions were administered under light isoflurane anesthesia using intravitreal injection or topical administration.

Intravitreal injection was performed as follows: Using a 30 gauge needle attached to a Hamilton syringe, 10 µL (0.01 mL) of the test composition was injected into the vitreous chamber of the eye once daily.

Topical administration was performed as follows: Two drops of 40 µL (two drops of 0.04 mL, or 0.08 mL total) of the test composition was applied to the corneal surface of the eye using an eye drop dispenser. Drops were applied to the chicks twice daily.

To determine changes in the rate of eye growth and the development of myopia, changes in axial length and refraction were assessed. Myopia is associated with excessive elongation of the eye in the axial direction relative to normal growth rates. Such excessive axial elongation leads to a relative myopic change in refraction. Axial length and refraction were measured using A-scan ultrasonography (Biometer AL-100; Tomey Corporation, Nagoya, Japan) and automated infrared photo-retinoscopy respectively. Statistical analysis of changes in both refraction and axial length between groups involved a one-way ANOVA test followed by a Student's T-test with Bonferroni correction. All data are presented as the mean±the standard deviation of the mean (SEM).

Results

Figure 2:
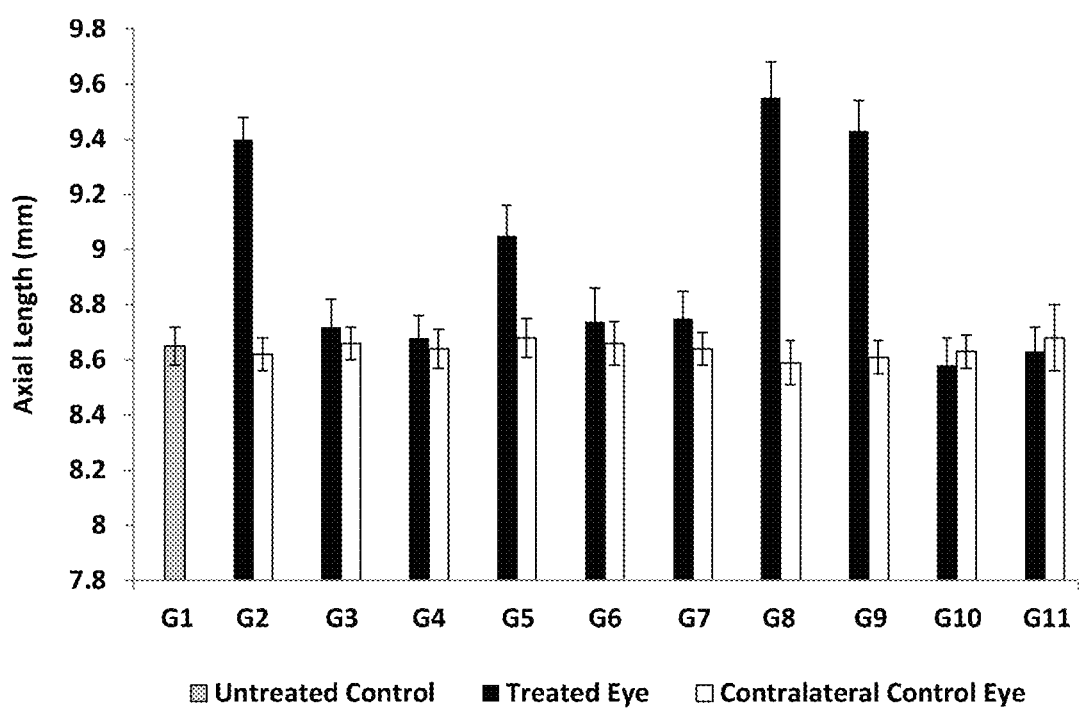
FIG. 2 shows the changes in axial length in chick eyes in response to diffuser-wear and treatment with levodopa/carbidopa compositions.

The results are presented in FIGS. 1 and 2. Attachment of a translucent diffuser over the left eye induced a significant myopic shift in refraction over a five day period (G2, FIG. 1) associated with excessive axial elongation (G2, FIG. 2), relative to that seen in contralateral control eyes (G2, FIGS. 1 and 2; refraction, $p<0.001$; axial length $p<0.001$) or age-matched untreated control eyes (G1, FIGS. 1 and 2; refraction, $p<0.001$; axial length $p<0.001$). There was no difference in the refractive development or axial length between contralateral control eyes of different treatment groups relative to each other (refraction $p=0.34$; axial length $p=0.39$) or age-matched untreated eyes (refraction $p=0.54$; axial length $p=0.42$).

Daily administration of levodopa/carbidopa compositions, through either intravitreal injection or topical administration, abolished the development of form-deprivation myopia over a five day period (G3, G4, G6 and G7, FIGS. 1 and 2). Specifically, the axial length of diffuser-treated eyes that were administered levodopa/carbidopa compositions daily via intravitreal injection or topical application (G3, G4, G6 and G7, FIG. 2), were not different to that seen in either contralateral control eyes (injection levodopa/carbidopa composition of Example 2, $p=0.38$; injection levodopa/carbidopa composition of Example 3, $p=0.22$; drops levodopa/carbidopa composition of Example 2, p=0.33; drops levodopa/carbidopa composition of Example 3, p=0.24) or age-matched untreated control eyes (injection levodopa/carbidopa composition of Example 2, p=0.27; injection levodopa/carbidopa composition of Example 3, p=0.18; drops levodopa/carbidopa composition of Example 2, p=0.26; drops levodopa/carbidopa composition of Example 3, p=0.19). Similarly, there was no significant difference in refractive development between eyes treated with diffusers plus levodopa/carbidopa compositions (G3, G4, G6 and G7, FIG. 1) relative to either contralateral control (injection levodopa/carbidopa composition of Example 2, p=0.26; injection levodopa/carbidopa composition of Example 3, p=0.19; drops levodopa/carbidopa composition of Example 2, p=0.23; drops levodopa/carbidopa composition of Example 3, p=0.16) or age-matched untreated eyes (injection levodopa/carbidopa composition of Example 2, p=0.19; injection levodopa/carbidopa composition of Example 3, p=0.16; drops levodopa/carbidopa composition of Example 2, p=0.16; drops levodopa/carbidopa composition of Example 3, p=0.15). Therefore, eyes treated with compositions comprising levodopa and carbidopa showed neither increased axial elongation, nor a myopic shift in refraction in response to diffuser-wear.

Daily oral administration of levodopa and carbidopa for five days (G5, FIGS. 1 and 2) at an amount equivalent to that provided by topical application (10 mg/kg/day of levodopa and 2.5 mg/kg/day of carbidopa), reduced the development of FDM by roughly 50% relative to that seen in the FDM only group (G2) (axial length, p<0.05; refraction, p<0.05). This protection is significantly less than that seen in response to either intravitreal injection or topical administration of levodopa/carbidopa compositions, indicating that direct application to the eye is a more effective route of administration.

Injection or topical administration of the vehicle solution to diffuser-treated eyes for a five day period did not alter the development of FDM (G8 and G9, FIGS. 1 and 2). Furthermore, injection or topical application of levodopa/carbidopa compositions to otherwise untreated eyes (G10 and G11, FIGS. 1 and 2), did not alter axial growth (injection, p=0.63; drops, p=0.57) or refractive development (injection, p=0.71; drops, p=0.62), relative to that seen in age-matched untreated control eyes.

Example 5—Efficacy of Levodopa Compositions in Preventing Form Deprivation Myopia 32 male White Cockerel chickens were randomly assigned to one of 8 treatment groups (n=4 per group) as defined below and were treated for a five day period. G1-G8 represent the labelling system used in FIGS. 3 and 4.
G1. Age-matched untreated control group
G2. Chicks fitted with a translucent diffuser over their left eye to induce FDM
G3. Chicks fitted with a translucent diffuser over their left eye and daily intravitreal injection of the composition of Example 2
G4. Chicks fitted with a translucent diffuser over their left eye and daily intravitreal injection of the composition of Example 1
G5. Chicks fitted with a translucent diffuser over their left eye and daily topical administration of the composition of Example 2
G6. Chicks fitted with a translucent diffuser over their left eye and daily topical administration of the composition of Example 1
G7. Chicks fitted with a translucent diffuser over their left eye and daily oral administration of 10 mg/kg levodopa, 2.5 mg/kg carbidopa as a powder
G8. Chicks fitted with a translucent diffuser over their left eye and daily oral administration of 10 mg/kg levodopa Administration of the test compositions and analysis of their activity were as described in Example 4.

Results

Figure 3:
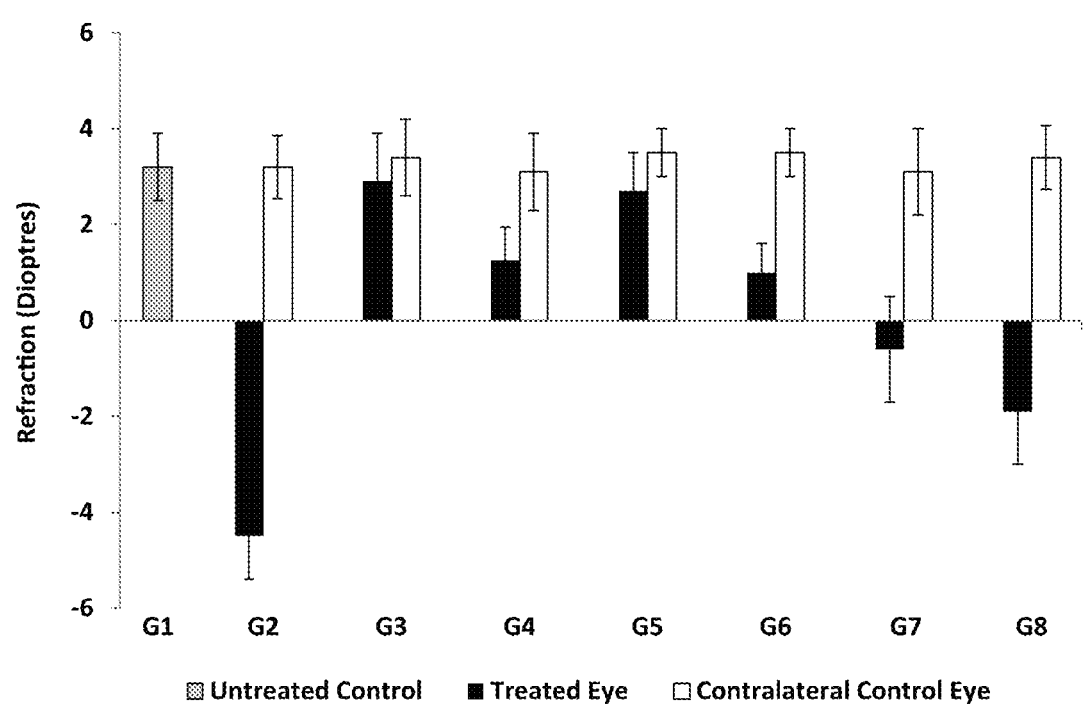
FIG. 3 shows the refractive development in chick eyes in response to diffuser-wear and treatment with levodopa or levodopa/carbidopa compositions.
Figure 4:
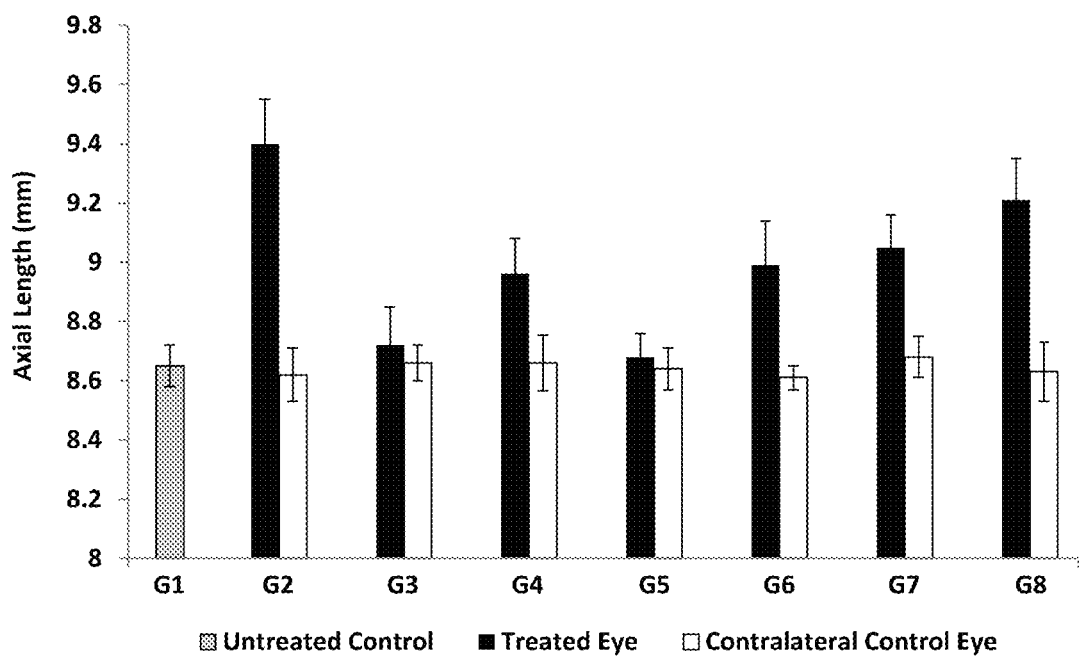
FIG. 4 shows the changes in axial length in chick eyes in response to diffuser-wear and treatment with levodopa or levodopa/carbidopa compositions.

The results are presented in FIGS. 3 and 4. Again, attachment of a translucent diffuser over the left eye induced a significant myopic shift in refraction (G2, FIG. 3) associated with excessive axial elongation (G2, FIG. 4), relative to that seen in contralateral control eyes (G2, FIGS. 3 and 4; refraction, p<0.001; axial length, p<0.001) or age-matched untreated control eyes (G1, FIGS. 3 and 4; refraction, p<0.001; axial length, p<0.001). There was no difference in the refractive development or axial length between contralateral control eyes of different treatment groups relative to each other (p=0.27) or age-matched untreated eyes (p=0.21).

Daily administration of levodopa/carbidopa compositions abolished the development of FDM, such that no differences were seen in the axial elongation or refractive development in response to diffuser-wear when compared with the contralateral control (refraction, p<0.01; axial length, p<0.01) or age-matched untreated (refraction, p<0.01; axial length, p<0.01) eyes (G3 and G5, FIGS. 3 and 4). Daily administration of levodopa compositions reduced the development of FDM when compared to the positive control (G2, FIGS. 3 and 4; refraction, p<0.05; axial length, p<0.05). However, this inhibition was to a significantly lower extent than compositions comprising the combination of levodopa and carbidopa.

Example 6—Method of Producing 0.003% W/V Levodopa Composition 0.12 mg levodopa was dissolved in a solution containing 0.15 M hydrochloric acid, 0.1% ascorbic acid and 1×PBS (solution is approximately pH 2). Once levodopa was dissolved, the solution was adjusted to a pH of 6 using sodium hydroxide to obtain a final volume of 4 mL.

Example 7—Method of Producing 0.03% W/V Levodopa Composition 1.2 mg levodopa was dissolved in a solution containing 0.15 M hydrochloric acid, 0.1% ascorbic acid and 1×PBS (solution is approximately pH 2). Once levodopa was dissolved, the solution was adjusted to a pH of 6 using sodium hydroxide to obtain a final volume of 4 mL.

Example 8—Method of Producing 0.03% W/V Levodopa, 10% V/V DMSO Composition 1.2 mg levodopa was dissolved in a solution containing 0.15 M hydrochloric acid, 0.1% ascorbic acid, 10% DMSO and 1×PBS. Once levodopa was dissolved, the solution was adjusted to a pH of 6 using sodium hydroxide to obtain a final volume of 4 mL.

Example 9—Method of Producing 0.3% W/V Levodopa, 10% V/V DMSO Composition 12 mg levodopa was dissolved in a solution containing 0.15 M hydrochloric acid, 0.1% ascorbic acid, 10% DMSO and 1×PBS. Once levodopa was dissolved, the solution was adjusted to a pH of 6 using sodium hydroxide to obtain a final volume of 4 mL.

Example 10—Method of Producing 0.03% W/V Levodopa, 0.03% W/V 2-Amino-6,7-Dihydroxy-1, 2,3,4-Tetrahydronaphthalene Hydrobromide (ADTN) Composition 1.2 mg levodopa (1.5 mM) was dissolved in a solution containing 0.15 M hydrochloric acid, 0.1% ascorbic acid and 1×PBS. Once levodopa was dissolved, the solution was adjusted to a pH of 6 using sodium hydroxide, and 1.2 mg ADTN (1 mM; in the form of 2-amino-6,7-dihydroxy-1,2, 3,4-tetrahydronaphthalene hydrobromide; commercially available from Sigma Aldrich Co. LLC) was dissolved in the solution to a final volume of 4 mL.

Example 11—Method of Producing 0.03% W/V Levodopa, 0.14% W/V Atropine Composition 1.2 mg levodopa (1.5 mM) was dissolved in a solution containing 0.15 M hydrochloric acid, 0.1% ascorbic acid and 1×PBS. Once levodopa was dissolved, the solution was adjusted to a pH of 6 using sodium hydroxide, and 5.6 mg atropine (2 mM; in the form of atropine sulfate salt monohydrate, commercially available from Sigma Aldrich Co. LLC) was dissolved in the solution to a final volume of 4 mL.

Example 12—Method of Producing 0.03% W/V Levodopa, 0.7% W/V Pirenzepine Composition 1.2 mg levodopa (1.5 mM) was dissolved in a solution containing 0.15 M hydrochloric acid, 0.1% ascorbic acid and 1×PBS. Once levodopa was dissolved, the solution was adjusted to a pH of 6 using sodium hydroxide, and 28 mg pirenzepine (16 mM; in the form of pirenzepine dihydrochloride, commercially available from Sigma Aldrich Co. LLC) was dissolved in the solution to a final volume of 4 mL.

Example 13—Effect of Levodopa Dose and Presence of DMSO on Prevention of Form Deprivation Myopia 120 male White Cockerel chickens were randomly assigned to one of 24 treatment groups (n=5 per group) as defined below and were treated for a five day period. G1-G24 represent the labelling system used in FIGS. 5-8.
G1. Age-matched untreated control group
G2. Chicks fitted with a translucent diffuser over their left eye to induce FDM
G3. Chicks fitted with a translucent diffuser over their left eye to induce FDM and daily oral administration of 20 mg/kg levodopa as a powder
G4. Chicks fitted with a translucent diffuser over their left eye to induce FDM and daily oral administration of 20 mg/kg levodopa and 5 mg/kg carbidopa as a powder
G5. Chicks fitted with a translucent diffuser over their left eye to induce FDM and daily intravitreal injection of the composition of Example 6 (0.003% w/v levodopa)
G6. Chicks fitted with a translucent diffuser over their left eye to induce FDM and daily intravitreal injection of the composition of Example 7 (0.03% w/v levodopa)
G7. Chicks fitted with a translucent diffuser over their left eye to induce FDM and daily intravitreal injection of the composition of Example 1 (0.3% w/v levodopa)
G8. Daily intravitreal injection of the composition of Example 1 (0.3% w/v levodopa)
G9. Chicks fitted with a translucent diffuser over their left eye to induce FDM and daily intravitreal injection of the composition of Example 3 (0.03% w/v levodopa, 0.008% w/v carbidopa)
G10. Chicks fitted with a translucent diffuser over their left eye to induce FDM and daily intravitreal injection of the composition of Example 2 (0.3% w/v levodopa, 0.08% w/v carbidopa)
G11. Daily intravitreal injection of the composition of Example 2 (0.3% w/v levodopa, 0.08% w/v carbidopa)
G12. Age-matched untreated control group
G13. Chicks fitted with a translucent diffuser over their left eye to induce FDM
G14. Chicks fitted with a translucent diffuser over their left eye to induce FDM and daily oral administration of 20 mg/kg levodopa as a powder
G15. Chicks fitted with a translucent diffuser over their left eye to induce FDM and daily oral administration of 20 mg/kg levodopa and 5 mg/kg carbidopa as a powder
G16. Chicks fitted with a translucent diffuser over their left eye to induce FDM and daily topical administration of the composition of Example 6 (0.003% w/v levodopa)
G17. Chicks fitted with a translucent diffuser over their left eye to induce FDM and daily topical administration of the composition of Example 7 (0.03% w/v levodopa)
G18. Chicks fitted with a translucent diffuser over their left eye to induce FDM and daily topical administration of the composition of Example 1 (0.3% w/v levodopa)
G19. Daily topical administration of the composition of Example 1 (0.3% w/v levodopa)
G20. Chicks fitted with a translucent diffuser over their left eye to induce FDM and daily topical administration of the composition of Example 3 (0.03% w/v levodopa, 0.008% w/v carbidopa)
G21. Chicks fitted with a translucent diffuser over their left eye to induce FDM and daily topical administration of the composition of Example 2 (0.3% w/v levodopa, 0.08% w/v carbidopa)
G22. Daily topical administration of the composition of Example 2 (0.3% w/v levodopa, 0.08% w/v carbidopa)
G23. Chicks fitted with a translucent diffuser over their left eye to induce FDM and daily topical administration of the composition of Example 8 (0.03% w/v levodopa, 10% DMSO)
G24. Chicks fitted with a translucent diffuser over their left eye to induce FDM and daily topical administration of the composition of Example 9 (0.3% w/v levodopa, 10% DMSO)

Administration of the test compositions and analysis of their activity were as described in Example 4.

Results

The results are presented in FIGS. 5 to 8. Attachment of a translucent diffuser over the left eye induced a significant myopic shift in refraction (G2, FIG. 5; and G13, FIG. 7; p<0.001) associated with excessive axial elongation (G2, FIG. 6; and G13, FIG. 8; p<0.001) relative to that seen in the age-matched untreated control eyes (G1, FIGS. 5 and 6; and G12, FIGS. 7 and 8).

Figure 5:
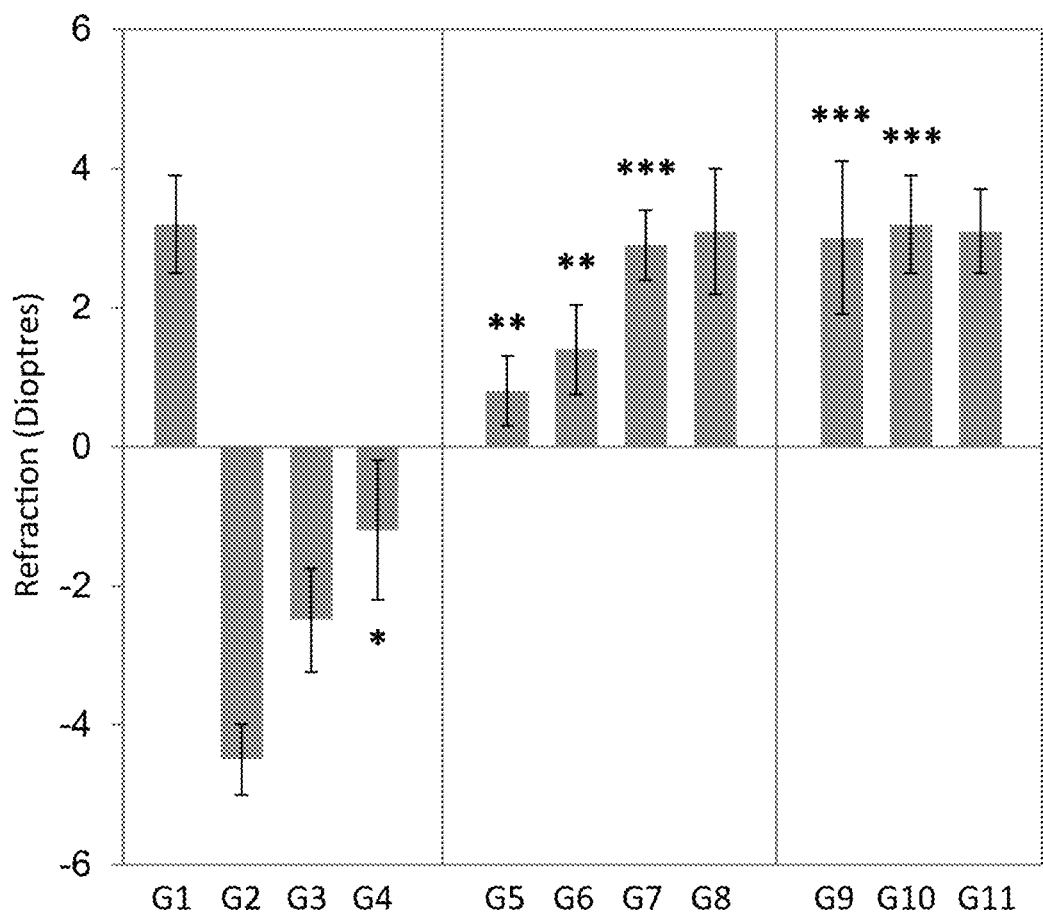
FIG. 5 shows the refractive development in chick eyes in response to diffuser-wear and intravitreal injection of levodopa or levodopa/carbidopa compositions. *=p<0.05; =p<0.01; *=p<0.001 relative to G2 (form deprivation myopia only).
Figure 6:
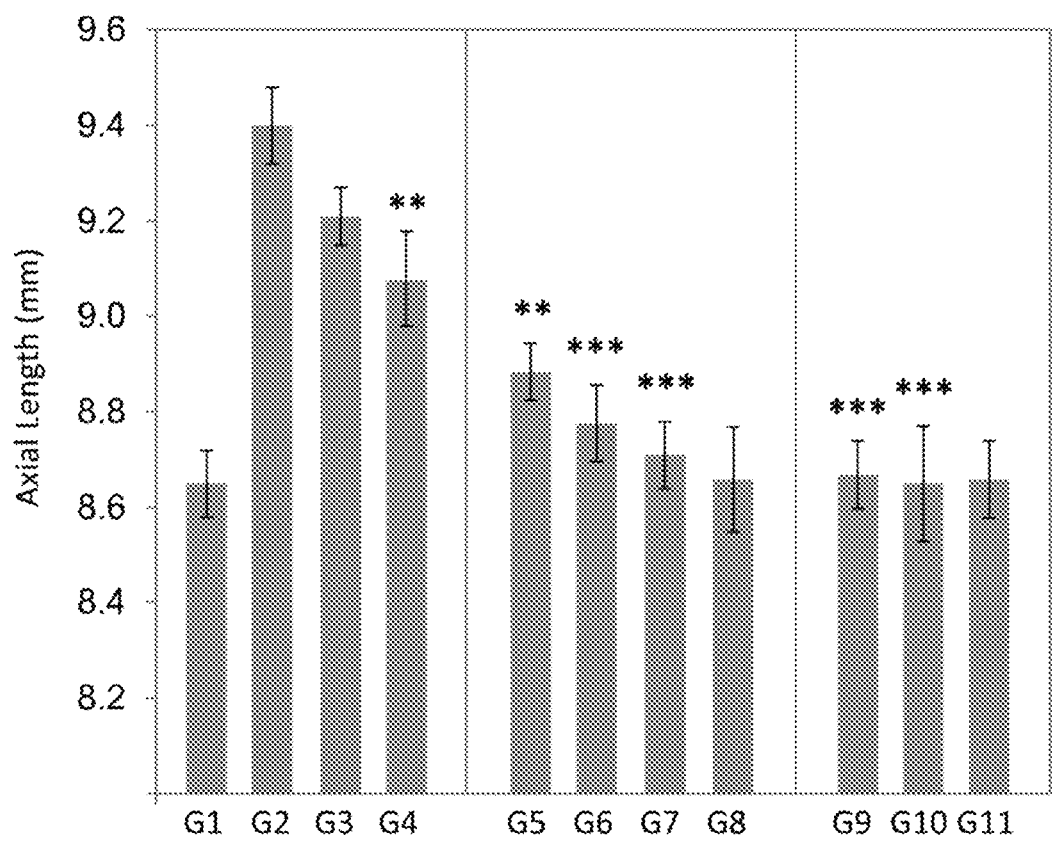
FIG. 6 shows the changes in axial length in chick eyes in response to diffuser-wear and intravitreal injection of levodopa or levodopa/carbidopa compositions. *=p<0.05; =p<0.01; *=p<0.001 relative to G2 (form deprivation myopia only).

Daily intravitreal injection of levodopa compositions significantly inhibited the development of FDM, with administration of a 0.3% w/v levodopa composition having the greatest effect (G5, p<0.01; G6, p<0.01; and G7, p<0.001; FIG. 5; and G5, p<0.01; G6, p<0.001; G7, p<0.001; FIG. 6). This effect was significantly greater than oral administration of levodopa (G3, FIGS. 5 and 6). Addition of the aromatic L-amino acid decarboxylase inhibitor, carbidopa, increased the inhibitory effect of the compositions (G9, p<0.01; and G10, p<0.01; FIG. 5; and G9, p<0.001; and G10, p<0.001; FIG. 6) in comparison with compositions comprising levodopa alone.

Figure 7:
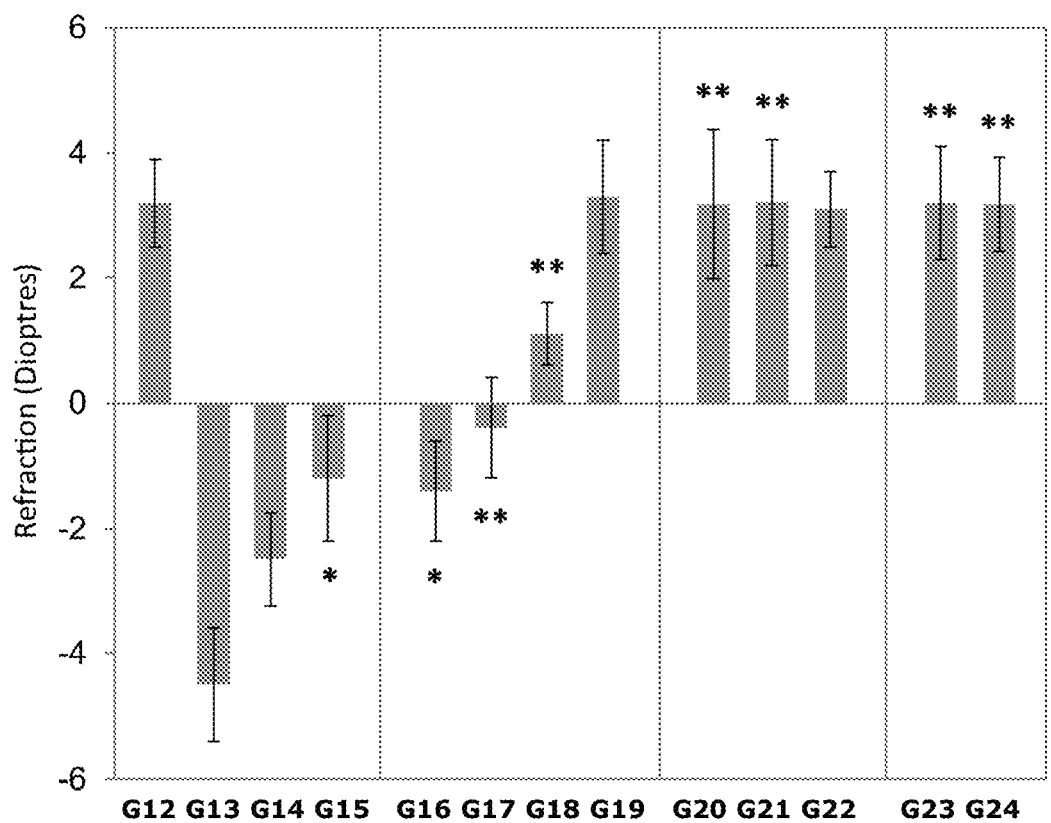
FIG. 7 shows the refractive development in chick eyes in response to diffuser-wear and topical administration of levodopa, levodopa/carbidopa or levodopa/DMSO compositions. *=p<0.05; =p<0.01; *=p<0.001 relative to G13 (form deprivation myopia only).
Figure 8:
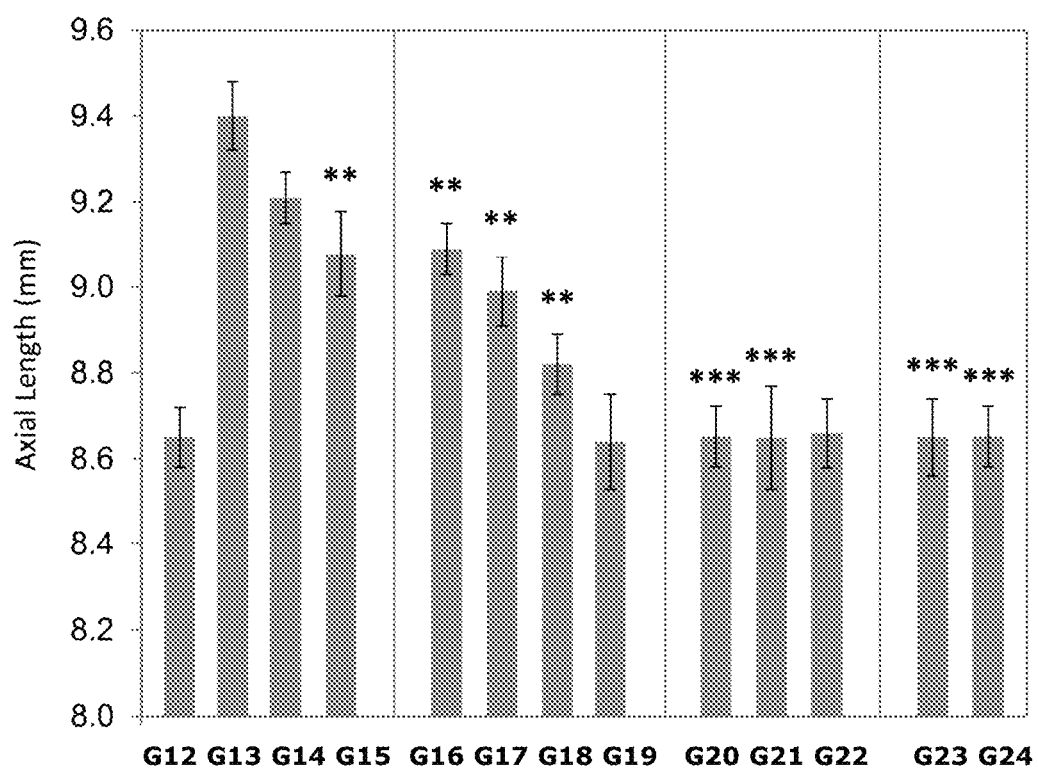
FIG. 8 shows the changes in axial length in chick eyes in response to diffuser-wear and topical administration of levodopa, levodopa/carbidopa or levodopa/DMSO compositions. *=p<0.05; =p<0.01; *=p<0.001 relative to G13 (form deprivation myopia only).

Daily topical administration of levodopa compositions significantly inhibited the development of FDM (G16, p<0.05; G17, p<0.01; and G18, p<0.01; FIG. 7; and G16, p<0.01; G17, p<0.01; and G18, p<0.01; FIG. 8) and demonstrated a stronger effect than oral levodopa administration (G14, FIGS. 7 and 8). Again, the addition of carbidopa to the compositions significantly increased the inhibitory effect (G20, p<0.01; and G21, p<0.01 FIG. 7; and G20, p<0.001; and G21, p<0.001; FIG. 8) in comparison with compositions comprising levodopa alone.

The addition of 10% DMSO to the topical levodopa compositions significantly increased the inhibitory effect against the development of FDM (G23, p<0.01; and G24, p<0.01; FIG. 7; and G23, p<0.001; and G24, p<0.001; FIG. 8) relative to the corresponding compositions comprising levodopa alone.

Example 14—Safety and Efficacy of Topical Levodopa Administration Over a Four Week Period To evaluate the safety and effectiveness of topical treatment of levodopa, twice daily eye-drop administration of a 15 mM (0.3% w/v) levodopa composition (prepared in accordance with Example 1) was tested over a period of four weeks. Male White Cockerel chickens were kept under normal laboratory light (500 lux, fluorescent lights) on a 12:12 hour light:dark cycle with lights on at 9:30 am and off at 9:30 pm. In all chicks, left eyes were treated experimentally while right eyes remained untreated to serve as a contralateral control. Chicks were randomly assigned to one of four groups (n=6 for each group) and treated over the four week period under the following experimental conditions:
1. Age-matched untreated controls: Chicks remained untreated, receiving no ocular or levodopa treatment
2. Form-deprivation myopia (FDM): Chicks were fitted with a translucent diffuser over their left eye to induce FDM, receiving no further treatment
3. Form-deprivation myopia and topical 0.3% w/v (15 mM) levodopa treatment: Chicks were fitted with a translucent diffuser over their left eye to induce FDM and were administered the composition of Example 1 topically twice daily (9:30 am and 2 pm)
4. Topical 0.3% w/v (15 mM) levodopa treatment to otherwise untreated eyes: Chicks were administered the composition of Example 1 topically twice daily (9:30 am and 2 pm)

Administration of the test compositions was performed in accordance with that described in Example 4.

To determine changes in the rate of eye growth and the development of myopia, axial length and refraction were measured using A-scan ultrasonography (Biometer AL-100; Tomey Corporation, Nagoya, Japan) and automated infrared photo-retinoscopy, respectively. Ocular measurements (axial length and refraction) were made on day one (prior to the commencement of experimentation) and every seven days for four weeks.

Results

Figure 9:
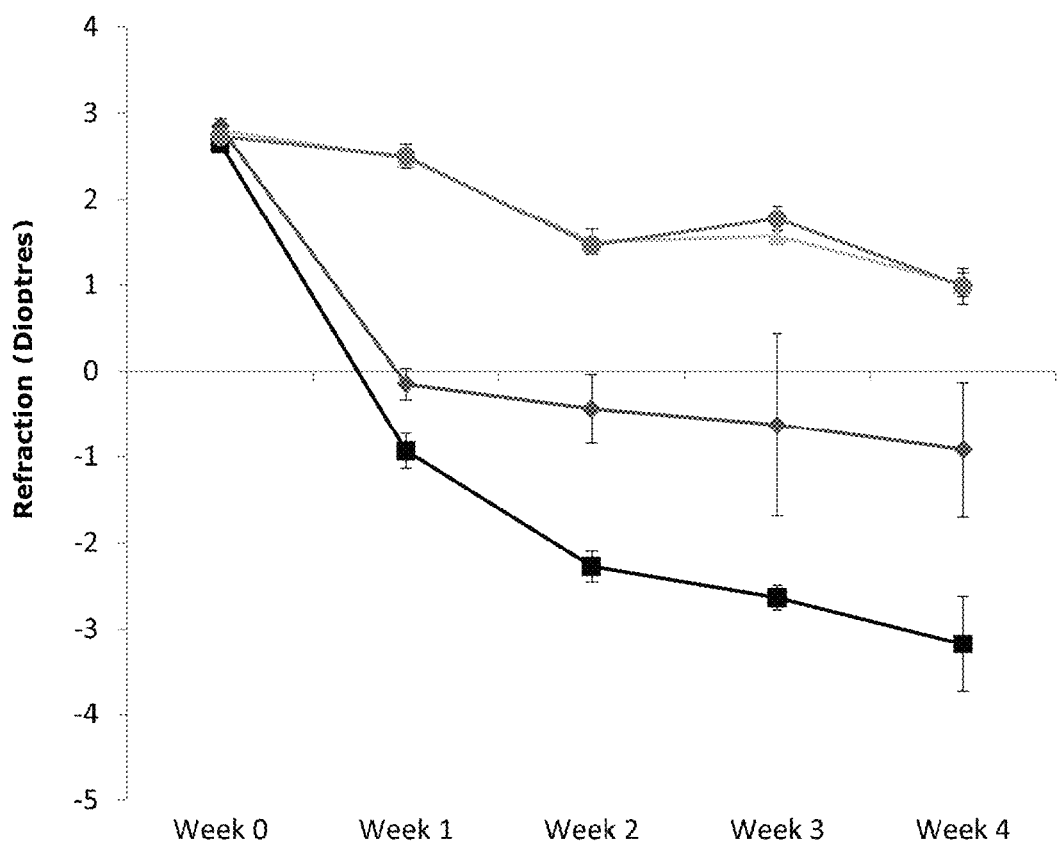
FIG. 9 shows the refractive development in chick eyes over a period of four weeks in response to diffuser-wear and topical administration of levodopa [※ =age-matched untreated control; ■=form-deprivation myopia; ◆=form-deprivation myopia and topical 0.3% w/v (15 mM) levodopa treatment; ✤=topical 0.3% w/v (15 mM) levodopa treatment to otherwise untreated eyes (no experimental myopia)].
Figure 10:
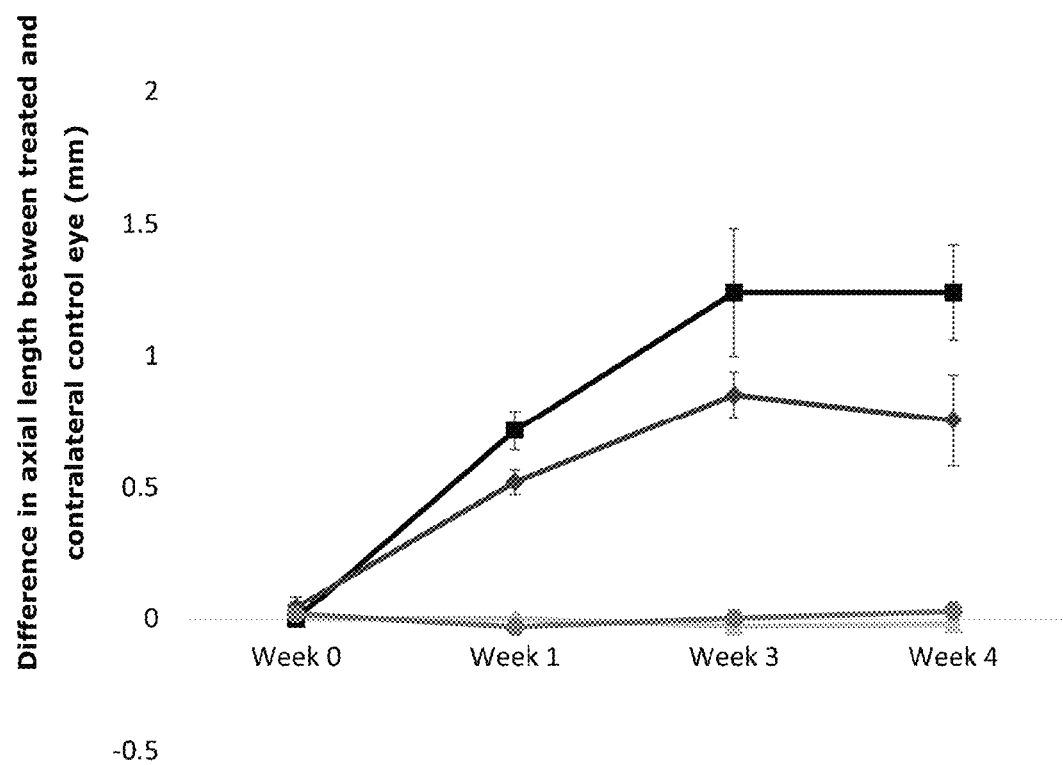
FIG. 10 shows the changes in axial length in chick eyes over a period of four weeks in response to diffuser-wear and topical administration of levodopa [※ =age-matched untreated control; ζ=form-deprivation myopia; ◆=form-deprivation myopia and topical 0.3% w/v (15 mM) levodopa treatment; ✤=topical 0.3% w/v (15 mM) levodopa treatment to otherwise untreated eyes (no experimental myopia)].

The results are presented in FIGS. 9 and 10. A multivariate analysis of variance (MANOVA) with repeated measures design was used to compare the effect of the different treatment regimens over time. Animals fitted with translucent diffusers and treated with topical levodopa saw a significantly smaller myopic shift in refraction in comparison to those animals fitted with translucent diffusers in the absence of levodopa treatment (FIG. 9; $F(3,21)=191.013$; $p<0.001$). Furthermore, animals fitted with translucent diffusers and treated with topical levodopa showed decreased axial elongation in comparison to those animals fitted with translucent diffusers in the absence of levodopa treatment (FIG. 10; $(F3,21)=34.129$; $p<0.001$).

Example 15—Effect of Co-Treatment of Levodopa with ADTN, Atropine and Pirenzepine on Form Deprivation Myopia Development 70 male White Cockerel chickens were randomly assigned to one of 14 treatment groups as defined below (n=5 per group) and were treated for a five day period. G1-G14 represent the labelling system used in FIGS. 11 and 12.
G1. Age-matched untreated control group
G2. Chicks fitted with a translucent diffuser over their left eye to induce FDM
G3. Chicks fitted with a translucent diffuser over their left eye to induce FDM and daily intravitreal injection of a composition containing 1 mM ADTN (0.03% w/v) and 0.1% ascorbic acid in 1×PBS (pH 7)
G4. Chicks fitted with a translucent diffuser over their left eye to induce FDM and daily topical administration of a composition containing 1 mM ADTN (0.03% w/v) and 0.1% ascorbic acid in 1×PBS (pH 7)
G5, G9 and G13. Chicks fitted with a translucent diffuser over their left eye to induce FDM and daily topical administration of the composition of Example 7 (0.03% w/v levodopa)
G6. Chicks fitted with a translucent diffuser over their left eye to induce FDM and daily topical administration of the composition of Example 10 (0.03% w/v levodopa, 0.03% w/v ADTN)
G7. Chicks fitted with a translucent diffuser over their left eye to induce FDM and daily intravitreal administration of a composition containing 2 mM atropine (0.14% w/v; in the form of atropine sulfate salt monohydrate) in distilled water (pH 7)
G8. Chicks fitted with a translucent diffuser over their left eye to induce FDM and daily topical administration of a composition containing 2 mM atropine (0.14% w/v; in the form of atropine sulfate salt monohydrate) in distilled water (pH 7)
G10. Chicks fitted with a translucent diffuser over their left eye to induce FDM and daily topical administration of the composition of Example 11 (0.03% w/v levodopa, 0.14% w/v atropine)
G11. Chicks fitted with a translucent diffuser over their left eye to induce FDM and daily intravitreal administration of a composition containing 16 mM pirenzepine (0.7% w/v; in the form of pirenzepine dihydrochloride) in distilled water (pH 7)
G12. Chicks fitted with a translucent diffuser over their left eye to induce FDM and daily topical administration of a composition containing 16 mM pirenzepine (0.7% w/v; in the form of pirenzepine dihydrochloride) in distilled water (pH 7)

G14. Chicks fitted with a translucent diffuser over their left eye to induce FDM and daily topical administration of the composition of Example 12 (0.03% w/v levodopa, 0.7% w/v pirenzepine)

ADTN compositions were prepared by dissolving ADTN in a solution containing 0.1% ascorbic acid in 1×PBS to a final concentration of 1 mM (0.03% w/v), and adjusting the pH to 7. Atropine and pirenzepine compositions were prepared by dissolving atropine (in the form of atropine sulfate salt monohydrate) or pirenzepine (in the form of pirenzepine dihydrochloride) in distilled water to a final concentration of 2 mM (0.14% w/v) and 16 mM (0.7% w/v), respectively, and adjusting the pH to 7.

Administration of test compositions and measurement of ocular parameters was performed in accordance with that described in Example 4.

Results

Figure 11:
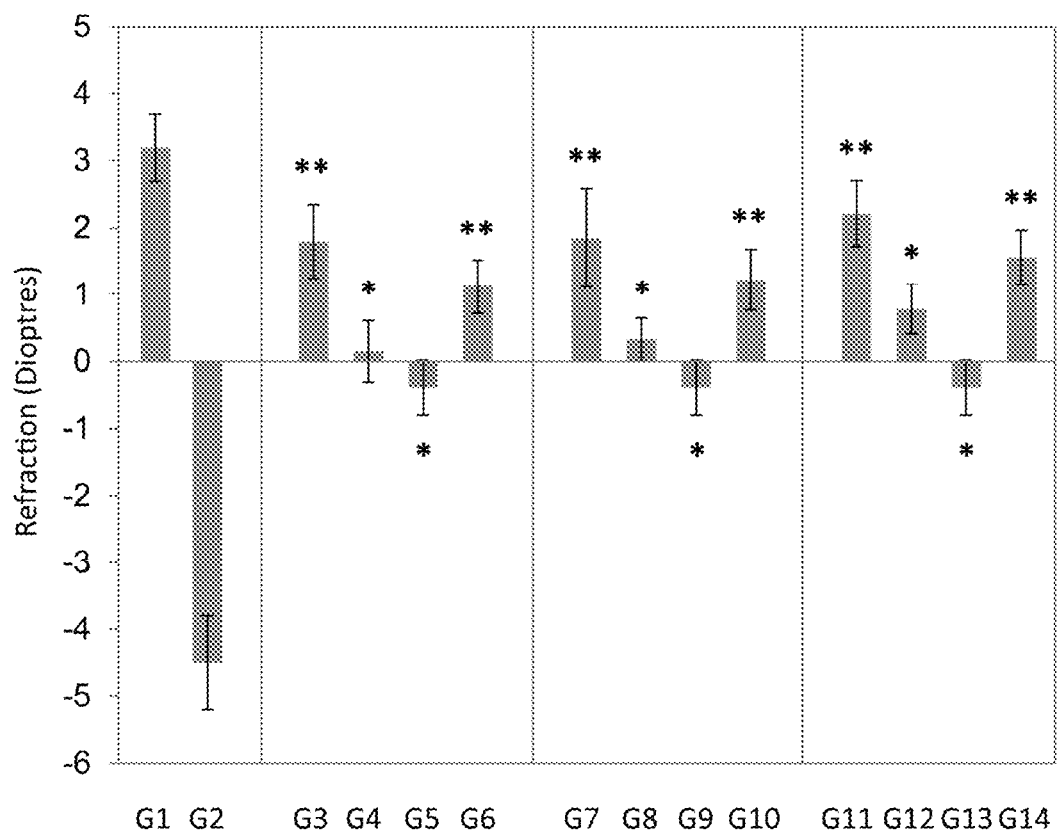
FIG. 11 shows the refractive development in chick eyes in response to diffuser-wear and topical administration of levodopa with ADTN, atropine and pirenzepine. *=p<0.05; **=p<0.01 relative to G2 (form deprivation myopia only).
Figure 12:
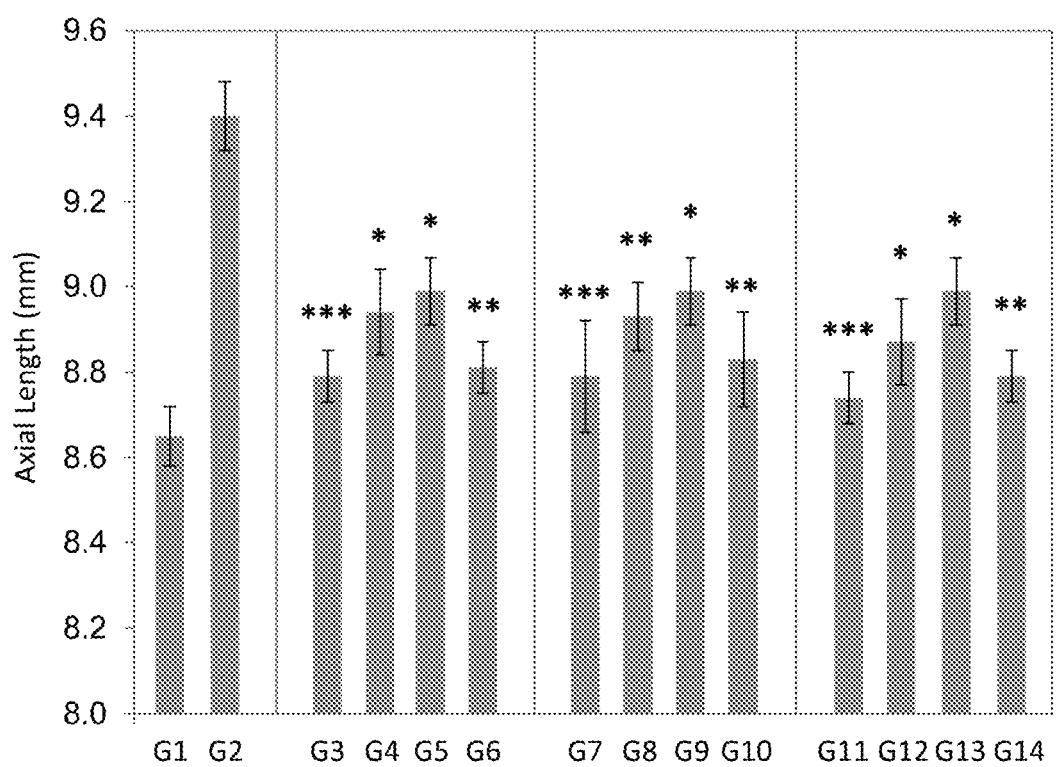
FIG. 12 shows the changes in axial length in chick eyes in response to diffuser-wear and topical administration of levodopa with ADTN, atropine and pirenzepine. *=p<0.05; =p<0.01; *=p<0.001 relative to G2 (form deprivation myopia only).

The results are presented in FIGS. 11 and 12. Daily administration of the dopamine D2 receptor agonist, ADTN (G3 and G4), significantly inhibited the myopic shift in refraction and decreased axial elongation in comparison with animals fitted with a translucent diffuser only (G2), with intravitreal injection having a greater effect than topical administration (G3, $p<0.01$; and G4, $p<0.05$; FIG. 11; G3, $p<0.001$; and G4, $p<0.05$; FIG. 12). Notably, topical administration of a composition comprising both ADTN and levodopa inhibited the myopic shift in refraction (G6, $p<0.01$; FIG. 11) and decreased axial elongation (G6, $p<0.01$; FIG. 12) to a greater extent than either compound alone (G4 and G5, respectively; FIGS. 11 and 12).

Daily administration of the muscarinic acetylcholine receptor antagonist, atropine (G7 and G8, FIGS. 11 and 12), significantly inhibited the myopic shift in refraction and decreased axial elongation in comparison with animals fitted with a translucent diffuser only (G2), with intravitreal injection having a greater effect than topical administration (G7, $p<0.01$; and G8, $p<0.05$; FIG. 11; G7, $p<0.001$; and G8, $p<0.05$; FIG. 12). Topical administration of a composition comprising both atropine and levodopa inhibited the myopic shift in refraction (G10, $p<0.01$; FIG. 11) and decreased axial elongation (G10, $p<0.01$; FIG. 12) to a greater extent than either compound alone (G8 and G9, respectively; FIGS. 11 and 12).

The M1 muscarinic acetylcholine receptor antagonist, pirenzepine (G11 and G12, FIGS. 11 and 12), significantly inhibited myopic shifts in refractive development and decreased axial elongation in comparison with animals fitted with a translucent diffuser only (G11, $p<0.01$; and G12, $p<0.05$; FIG. 11; G11, $p<0.001$; and G12, $p<0.05$; FIG. 12). The effects of pirenzepine were greater when intravitreally administered (G11, FIGS. 11 and 12). Topical administration of the combination of pirenzepine and levodopa (G14, FIGS. 11 and 12) had a greater inhibitory effect than topical administration of either compound alone on refractive development (G14, $p<0.01$; FIG. 11) and axial length (G14, $p<0.01$; FIG. 12).

Example 16—Histological Analysis of Effects of Topical Levodopa Administration on Form Deprivation Myopia Development For base histological analysis using toluidine blue staining, paraformaldehyde fixed retinal sections were immersed in an aqueous 1% toluidine blue (Sigma Aldrich, Catalogue No. 89640) solution for 1.5 minutes prior to rinsing under running distilled water for 2 minutes. Sections were then mounted in glycerol before cover slipping. Sections were viewed on a Motic BA410 light microscope at 40× magnification and captured by a Moticam 10.0 megapixel camera in conjunction with the Motic Live Imaging Module.

Retinal sections were from eyes of male White Cockerel chickens as follows:

A. Contralateral control eye of chick, wherein the other eye is fitted with a translucent diffuser to induce FDM B. Eye of chick fitted with a translucent diffuser to induce FDM C. Contralateral control eye of chick, wherein the other eye is fitted with a translucent diffuser to induce FDM and is treated with daily topical administration of the composition of Example 1 (0.3% w/v levodopa)

D. Eye of chick fitted with a translucent diffuser to induce FDM and treated with daily topical administration of the composition of Example 1 (0.3% w/v levodopa)

E. Contralateral control eye of chick, wherein the other eye is treated with daily topical administration of the composition of Example 1 (0.3% w/v levodopa)

F. Eye of chick treated with daily topical administration of the composition of Example 1 (0.3% w/v levodopa)

G. Eye of age-matched untreated control chick

Administration of levodopa compositions was performed in accordance with that described in Example 4.

Results

Figure 13:
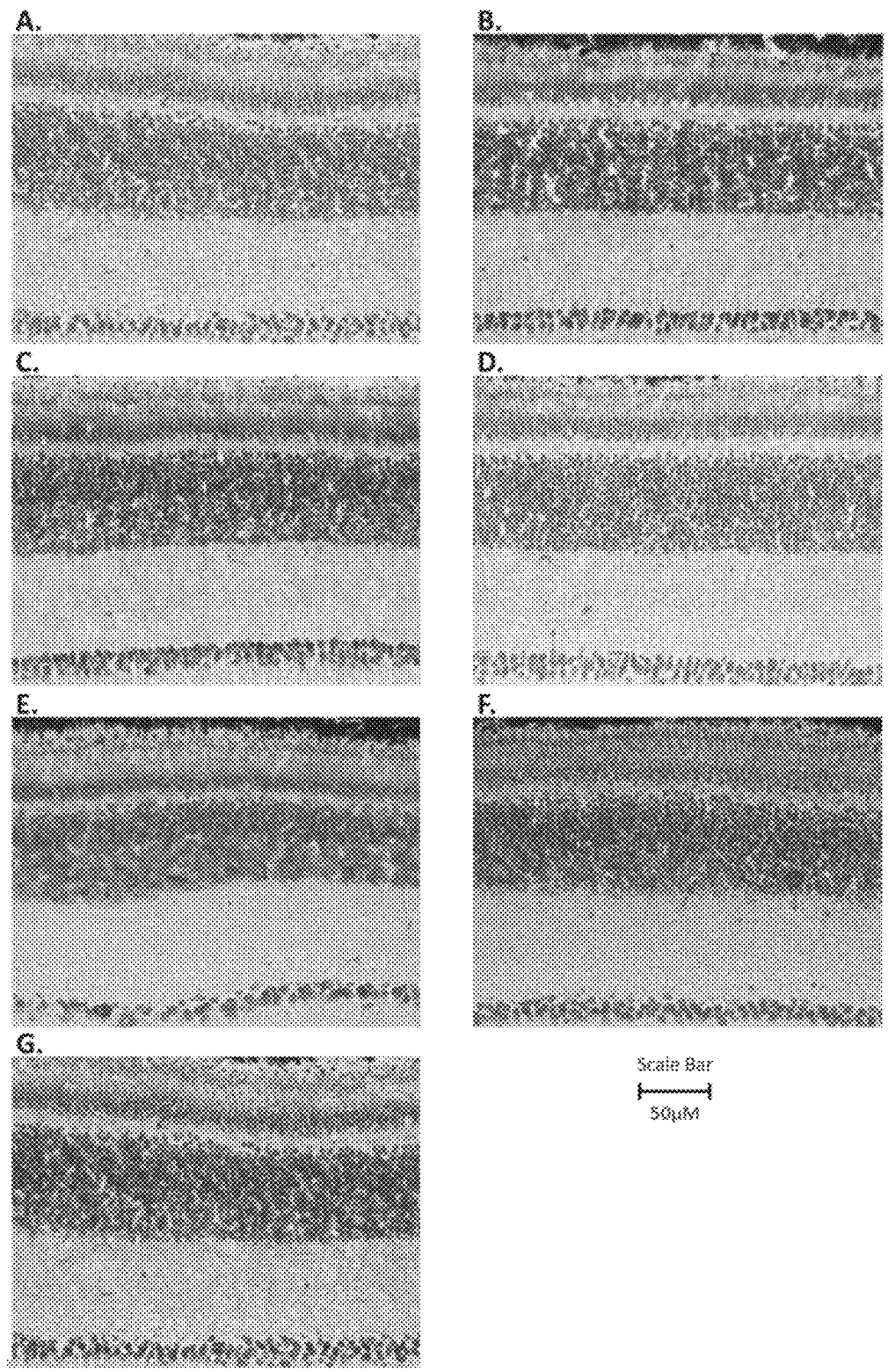
FIG. 13 shows the histological analysis of retinae from chick eyes stained with 1% toluidine blue after diffuser-wear and four weeks of topical levodopa treatment.

The results are presented in FIG. 13. As can be seen in FIG. 13, no alteration in retinal architecture or cell density was seen in the eyes of the following groups: age-matched untreated control (FIG. 13G), form-deprived (FIG. 13B), contralateral untreated control eyes of all conditions (FIGS. 13A, 13C and 13E), form-deprived and daily topical administration of a composition comprising 0.3% w/v levodopa (FIG. 13D), and daily topical administration of a composition comprising 0.3% w/v levodopa into otherwise untreated animals (FIG. 13F). Thus, the levodopa compositions do not display retinal toxicity.

Example 17—TUNEL Staining Analysis of Effects of Topical Levodopa Administration on Form Deprivation Myopia Development TUNEL staining was undertaken using the Roche In Situ Cell Death Detection Kit, AP (Sigma Aldrich, Catalogue No. 11684795910). The protocol used for staining retinal sections from male White Cockerel chickens was adapted from the work of Denton and Kumar (2015) *Cold Spring Harb Protoc*; doi:10.1101/pdb.prot086199. In short, retinal sections were prepared by washing in three changes of 1×PBS in 0.1% Triton X-100 (1×PBST), permeabilizing in 0.1% sodium citrate on ice for five minutes, followed by washing in three more changes of 1×PBST. Sections were then incubated in TUNEL Reaction Mixture according to the manufacturer's instructions (negative controls were incubated in Labelling Mixture only, whilst positive controls were incubated in DNase 1 (100 U/mL) for 10 minutes prior to TUNEL labelling to induce DNA fragmentation like that observed in apoptosis). Following TUNEL labelling, sections were washed in the dark in three changes of 1×PBS, followed by visualization using a Leica DMIL fluorescent microscope at 20× magnification with images captured by a Leica DFC425 camera using the Leica Application Suite version 4.8.

Analysed samples were as follows:
A. Negative control (retinal section treated with labelling solution only)
B. Positive control (retinal section treated with DNase 1 to induce DNA strand breakage, which is indicative of apoptosis)
C. Retinal section from eye of age-matched untreated control chick
D. Retinal section from eye of chick fitted with a translucent diffuser to induce FDM
E. Retinal section from eye of chick treated with daily topical administration of the composition of Example 1 (0.3% w/v levodopa)
F. Retinal section from eye of chick fitted with a translucent diffuser to induce FDM and treated with daily topical administration of the composition of Example 1 (0.3% w/v levodopa)

Administration of levodopa compositions was performed in accordance with that described in Example 4.

Results

Figure 14:
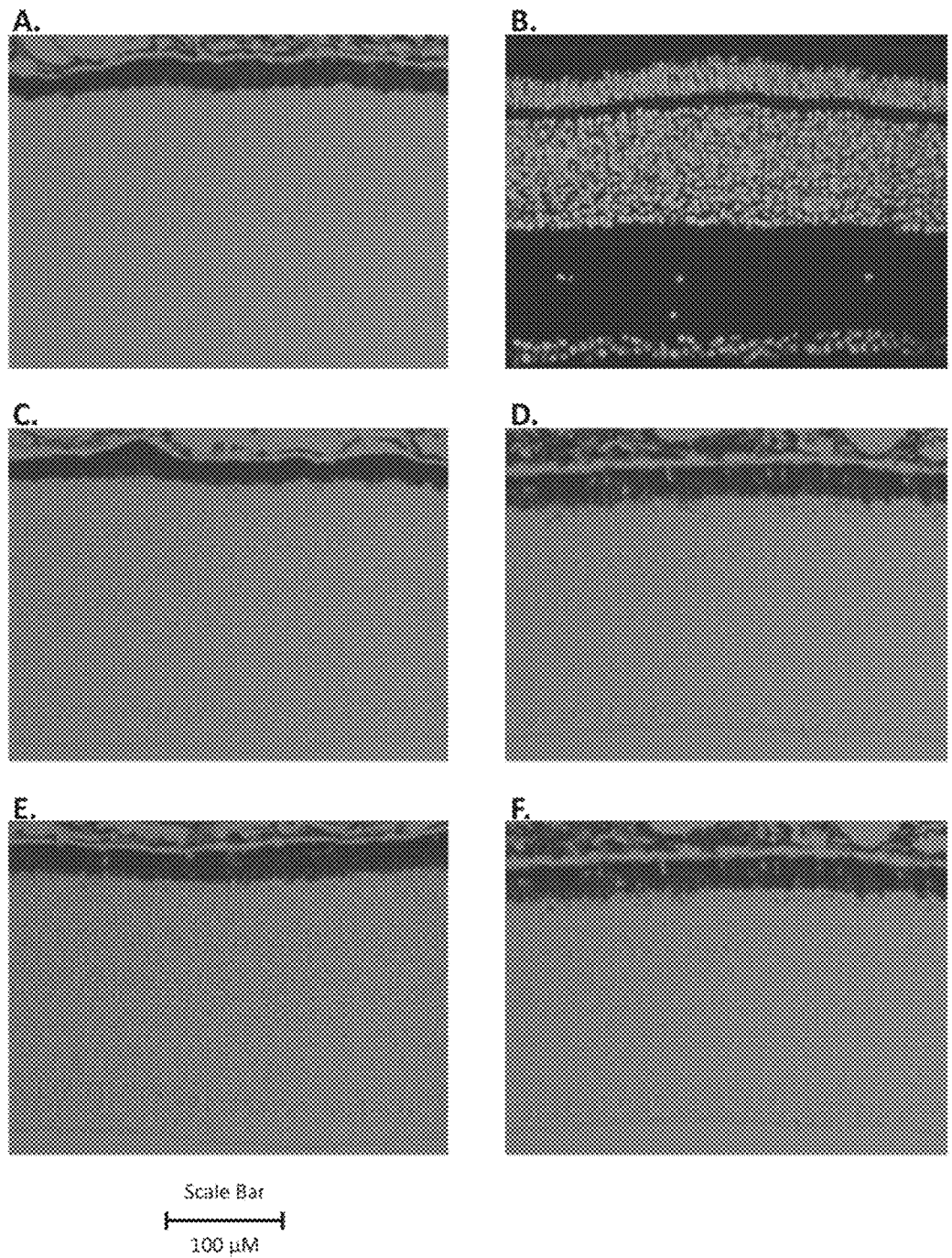
FIG. 14 shows the TUNEL assay analysis of retinae from chick eyes after diffuser wear and four weeks of topical levodopa treatment.

As can be seen in FIG. 14, retinal cells do not show signs of apoptosis in response to form-deprivation (FIG. 14D) or levodopa treatment (FIGS. 14E and 14F) when compared to positive control retinal tissue treated with DNase 1 to induce DNA nicks and genomic degradation (FIG. 14B). Due to no staining being present, visualization required over exposure of all but the positive control retinal sections, leading to the lighter appearance observed.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

What is claimed is:

1. A pharmaceutical ocular composition, comprising levodopa, a muscarinic acetylcholine receptor antagonist, an antioxidant and an aqueous carrier.

2. The composition according to claim 1, wherein the antioxidant is selected from the group consisting of ascorbic acid, phenolic acids, sorbic acid, sodium bisulfate, sodium metabisulfite, acetyl cysteine, sodium thiosulfate, ethylene diamine tetraacetic acid, sodium nitrite, ascorbyl stearate, ascorbyl palmitate, alpha-thioglycerol, erythorbic acid, cysteine hydrochloride, citric acid, tocopherol or vitamin E, tocopherol acetate, dibutylhydroxytoluene, soybean lecithin, sodium thioglycolate, butylhydroxyanisole, propyl gallate, uric acid, melatonin, thiourea, and salts and combinations thereof.

3. The composition according to claim 2, wherein the antioxidant is ascorbic acid.

4. The composition according to claim 1, further comprising an inhibitor of aromatic L-amino acid decarboxylase.

5. The composition according to claim 4, wherein the inhibitor of aromatic L-amino acid decarboxylase is selected from carbidopa, benserazide, methyldopa and combinations thereof.

6. The composition according to claim 5, wherein the inhibitor of aromatic L-amino acid decarboxylase is carbidopa.

7. The composition according to claim 4, wherein the ratio of levodopa to the inhibitor of aromatic L-amino acid decarboxylase is in the range of from 20:1 to 1:1.

8. The composition according to claim 1, wherein the composition further comprises a dopamine receptor agonist.

9. The composition according to claim 8, wherein the dopamine receptor agonist is selected from the group consisting of quinpirole, apomorphine, ropinirole, pramipexole, dexpramipexole, piribedil, rotigotine, bromocriptine, lisuride, cabergoline, 2-amino-6,7-dihydroxy-1,2,3,4-tetrahydronaphthalene, pergolide, calidopa, dihydrexidine, doxathrine, propylnorapomorphine, quinagolide, roxindole, sumanirole, fenoldopam, ergocornine, 1-phenyl-2,3,4,5-tetrahydro-(1H)-3-benzazepine-7,8-diol, 2-(N-phenethyl-N-propyl)amino-5-hydroxytetralin, dihydroergotamine, (1R,3 5)-1-(aminomethyl)-3-phenyl-3,4-dihydro-1H-isochromene-5,6-diol, carmoxirole, fenoldopam, and salts and combinations thereof.

10. The composition according to claim 1, wherein the composition further comprises a GABA receptor antagonist.

11. The composition according to claim 10, wherein the GABA receptor antagonist is selected from the group consisting of bicuculline, flumazenil, gabazine, phenylenetetrazol, (1,2,5,6-tetra hydropyridin-4-yl) methylphosphinic acid, (3-aminopropyl)(cyclohexylmethyl)phosphinic acid, and salts and combinations thereof.

12. The composition according to claim 1, wherein the muscarinic acetylcholine receptor antagonist is selected from the group consisting of atropine, pirenzepine, himbacine, hyoscine, cyclopentolate, ipratropium, oxitropium, tropicamide, oxybutynin, tolterodine, diphenhydramine, dicycloverine, flavoxate, tiotropium, trihexyphenidyl, solifenacin, darifenacin, benzatropine, mebeverine, procyclidine, aclidinium, and salts and combinations thereof.

13. The composition according to claim 1, wherein the aqueous carrier is selected from the group consisting of saline, water, aqueous buffer, an aqueous solution comprising water and a miscible solvent, and combinations thereof.

14. The composition according to claim 1, wherein the pH of the composition is in the range of from 5.5 to 6.

15. The composition according to claim 1, wherein the composition is formulated for topical administration to the eye.

16. A method of inhibiting the progression or development of a visual disorder in a subject, comprising administering to the subject the composition according to claim 1.

17. The method according to claim 16, wherein the visual disorder is selected from the group consisting of a visual disorder associated with diabetic retinopathy, and myopia.

18. The method according to claim 17, wherein the visual disorder is myopia.

19. A process for preparing the composition according to claim 1, comprising dissolving levodopa in the aqueous carrier at a pH in the range of from 0.5 to 2.5, adding the antioxidant and muscarinic acetylcholine receptor antagonist to the composition and adjusting the pH of the composition to a pH in the range of from 5 to 8.

20. The composition according to claim 1, wherein the composition comprises the levodopa and the muscarinic acetylcholine receptor antagonist in a weight ratio of from 1:4 to 1:23.

21. The composition according to claim 1, wherein the muscarinic acetylcholine receptor antagonist is atropine.

* * * * *